(12) United States Patent
Turi et al.

(10) Patent No.: US 7,037,299 B2
(45) Date of Patent: May 2, 2006

(54) DISPOSABLE ELASTIC ABSORBENT ARTICLE HAVING RETAINING ENCLOSURES

(75) Inventors: Mordechai Turi, Mill Hall, PA (US); Michael Kauschke, Yonkers, NY (US)

(73) Assignee: First Quality Products, Inc., State College, PA (US)

( * ) Notice: Subject to any disclaimer, the term of this patent is extended or adjusted under 35 U.S.C. 154(b) by 0 days.

(21) Appl. No.: 10/900,634

(22) Filed: Jul. 28, 2004

(65) Prior Publication Data
US 2005/0055004 A1   Mar. 10, 2005

Related U.S. Application Data

(63) Continuation of application No. 09/176,634, filed on Oct. 22, 1998, now abandoned, which is a continuation-in-part of application No. 09/097,198, filed on Jun. 12, 1998, now Pat. No. 6,413,249.

(51) Int. Cl.
A61F 13/15   (2006.01)

(52) U.S. Cl. .............................. 604/385.19; 604/385.24

(58) Field of Classification Search ........... 604/385.01, 604/385.19, 385.24, 385.25, 385.27, 385.29, 604/385.26, 385.28, 385.3
See application file for complete search history.

(56) References Cited

U.S. PATENT DOCUMENTS

| 5,087,255 A | | 2/1992 | Sims | |
|---|---|---|---|---|
| 5,330,598 A | * | 7/1994 | Erdman et al. | ............. 156/164 |
| 5,344,516 A | * | 9/1994 | Tanji et al. | ................. 156/164 |
| 5,380,310 A | * | 1/1995 | Mitrani | ................ 604/385.201 |
| 5,439,459 A | | 8/1995 | Tanji et al. | |
| 5,601,543 A | | 2/1997 | Dreier et al. | |
| 5,649,918 A | | 7/1997 | Schleinz | |
| 5,817,086 A | | 10/1998 | Kling | |
| 5,824,172 A | | 10/1998 | Kielpikowski | |
| 6,306,121 B1 | * | 10/2001 | Damaghi et al. | ...... 604/385.03 |
| 6,413,249 B1 | * | 7/2002 | Turi et al. | .................. 604/387 |
| 6,494,872 B1 | * | 12/2002 | Suzuki et al. | .......... 604/385.26 |
| 2003/0158534 A1 | * | 8/2003 | Niki et al. | ............. 604/385.25 |
| 2004/0143233 A1 | * | 7/2004 | Nakajima et al. | ..... 604/385.101 |
| 2004/0260261 A1 | * | 12/2004 | Yoshida et al. | .......... 604/385.3 |

FOREIGN PATENT DOCUMENTS

| EP | 1 106 152 A1 | * | 6/2001 |
|---|---|---|---|
| GB | 2 287 888 A | | 10/1994 |
| GB | 2 295 306 A | | 5/1996 |
| GB | 2 329 842 A | | 4/1999 |
| JP | 01077607 | | 3/1989 |
| WO | WO 95/25493 | | 9/1995 |
| WO | WO 98/37847 | | 9/1998 |
| WO | WO 99/16398 | | 4/1999 |

* cited by examiner

Primary Examiner—Tatyana Zalukaeva
Assistant Examiner—Michael G. Bogart
(74) Attorney, Agent, or Firm—Amster, Rothstein & Ebenstein LLP

(57) ABSTRACT

An integral disposable elasticized absorbent article has a front waist portion, a back waist portion, a crotch portion, a pair of spaced apart leg openings, an absorbent core member, and means for tightly fitting the absorbent body to the body of the wearer. The absorbent article has a barrier layer which comprises one or more segments overlying portions of the absorbent core member, and defining one or more retaining enclosures between the barrier layer segments and the underlying portion of the absorbent core member.

22 Claims, 27 Drawing Sheets

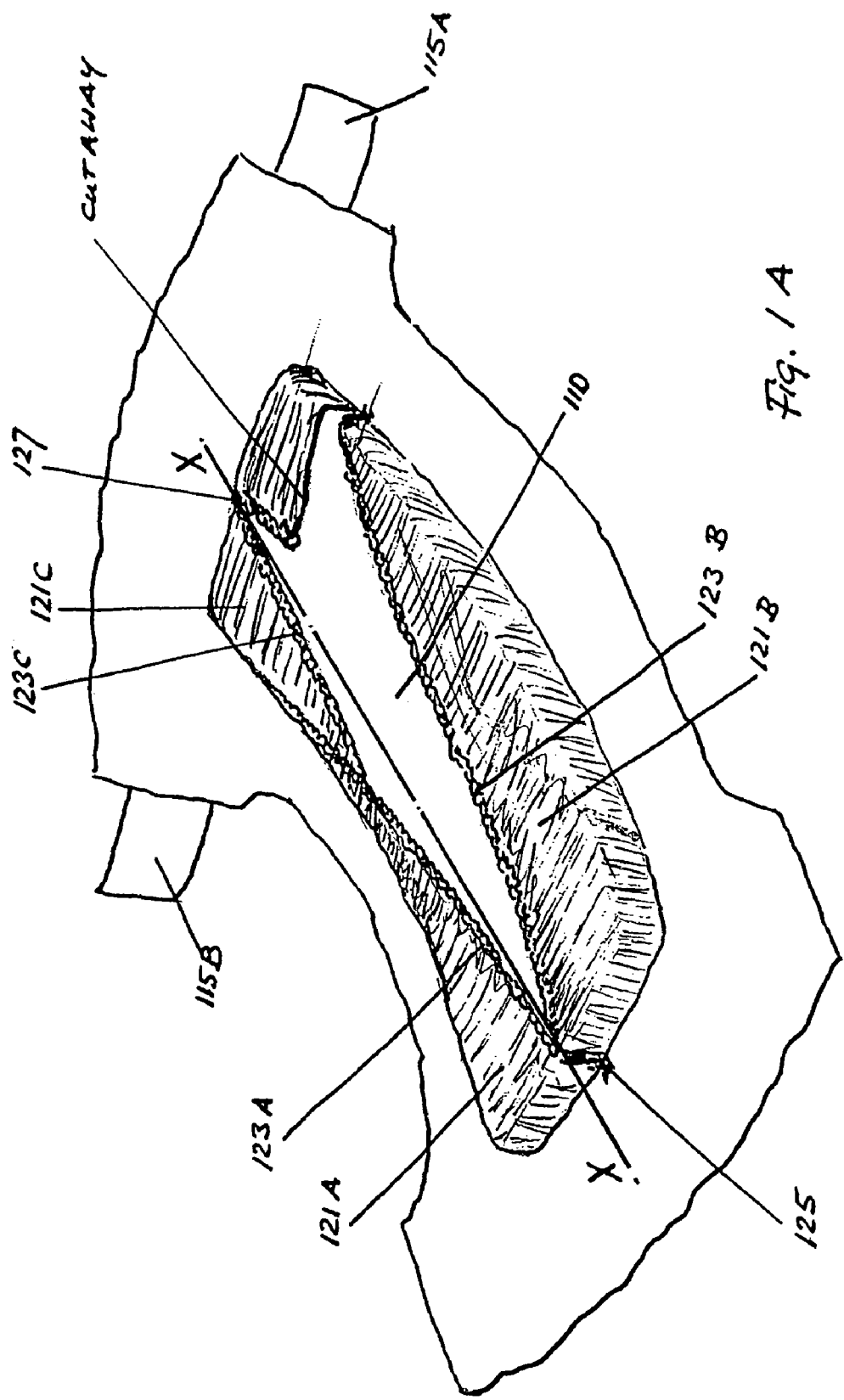

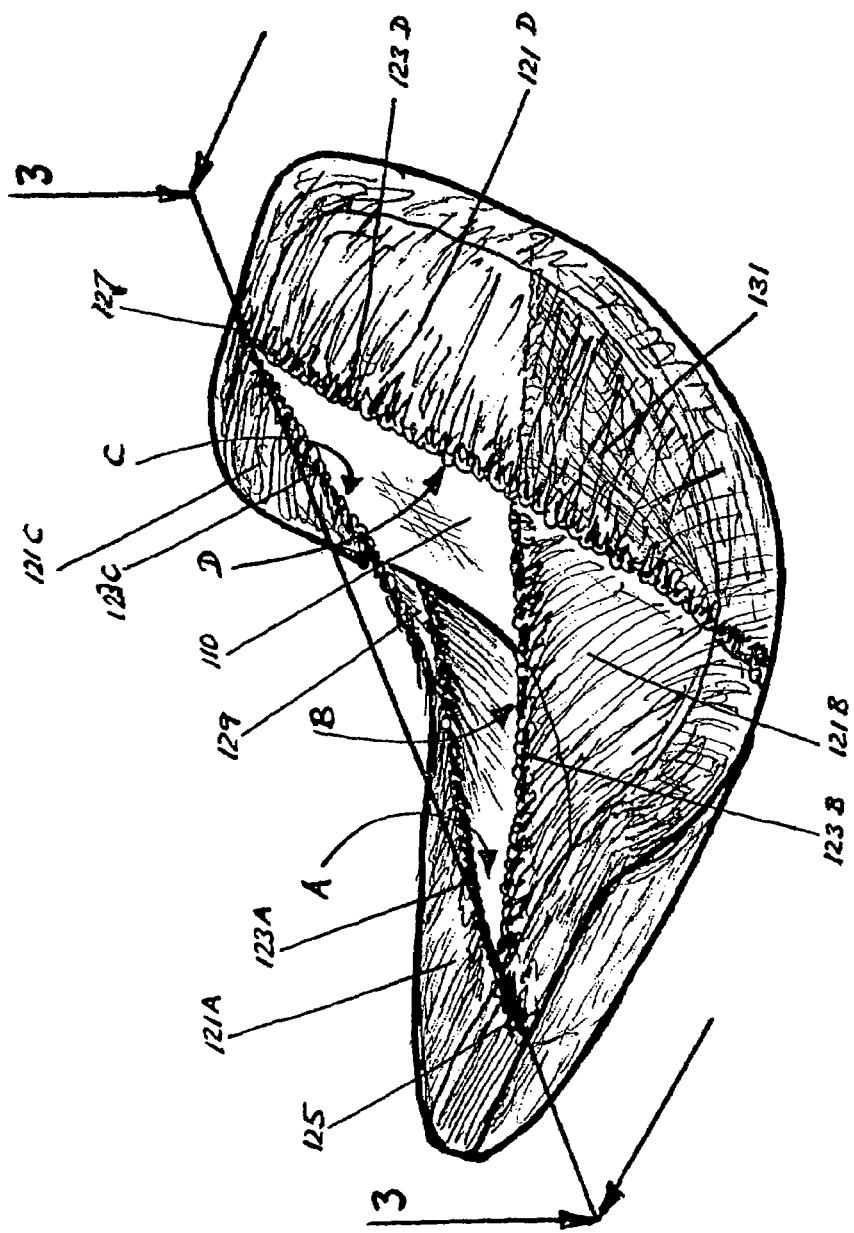

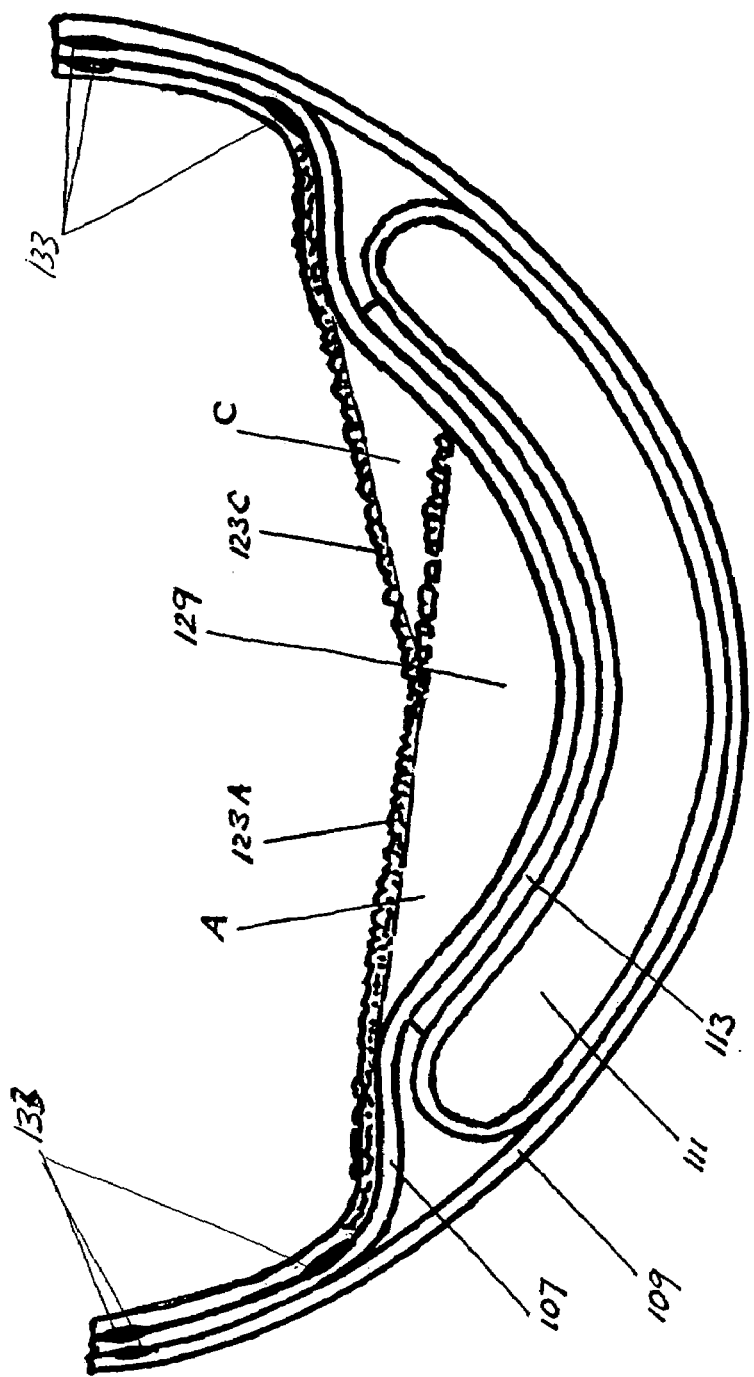

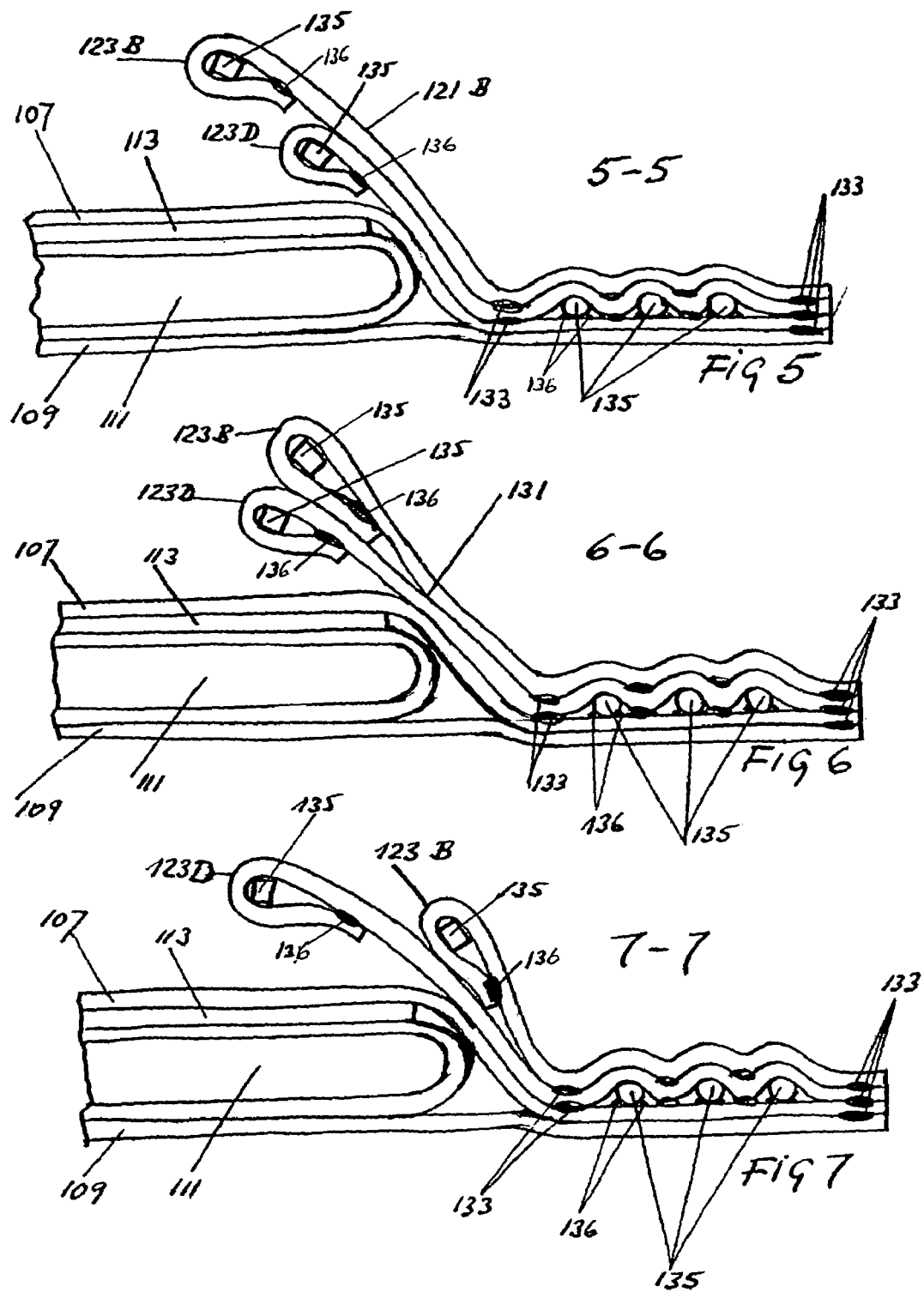

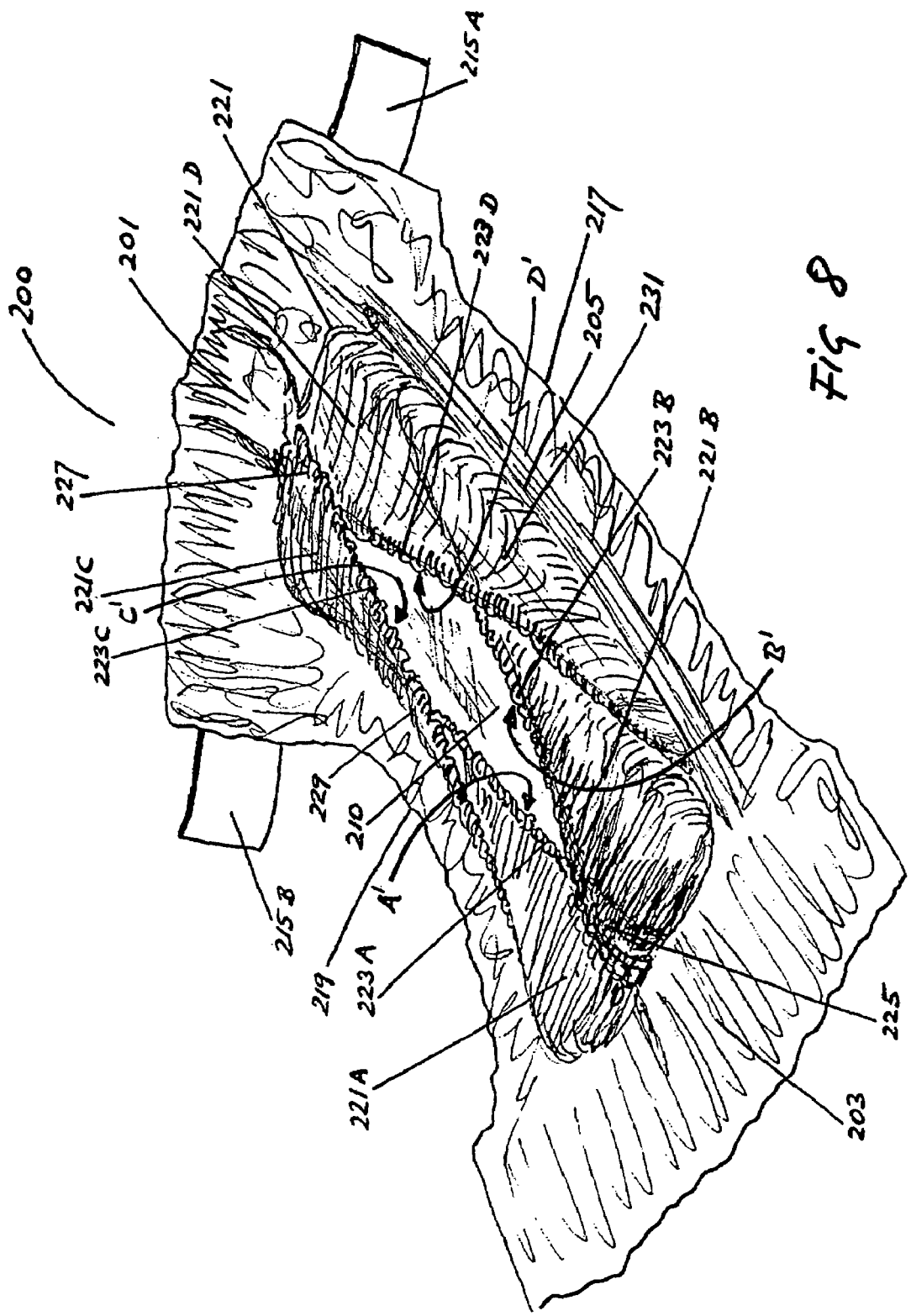

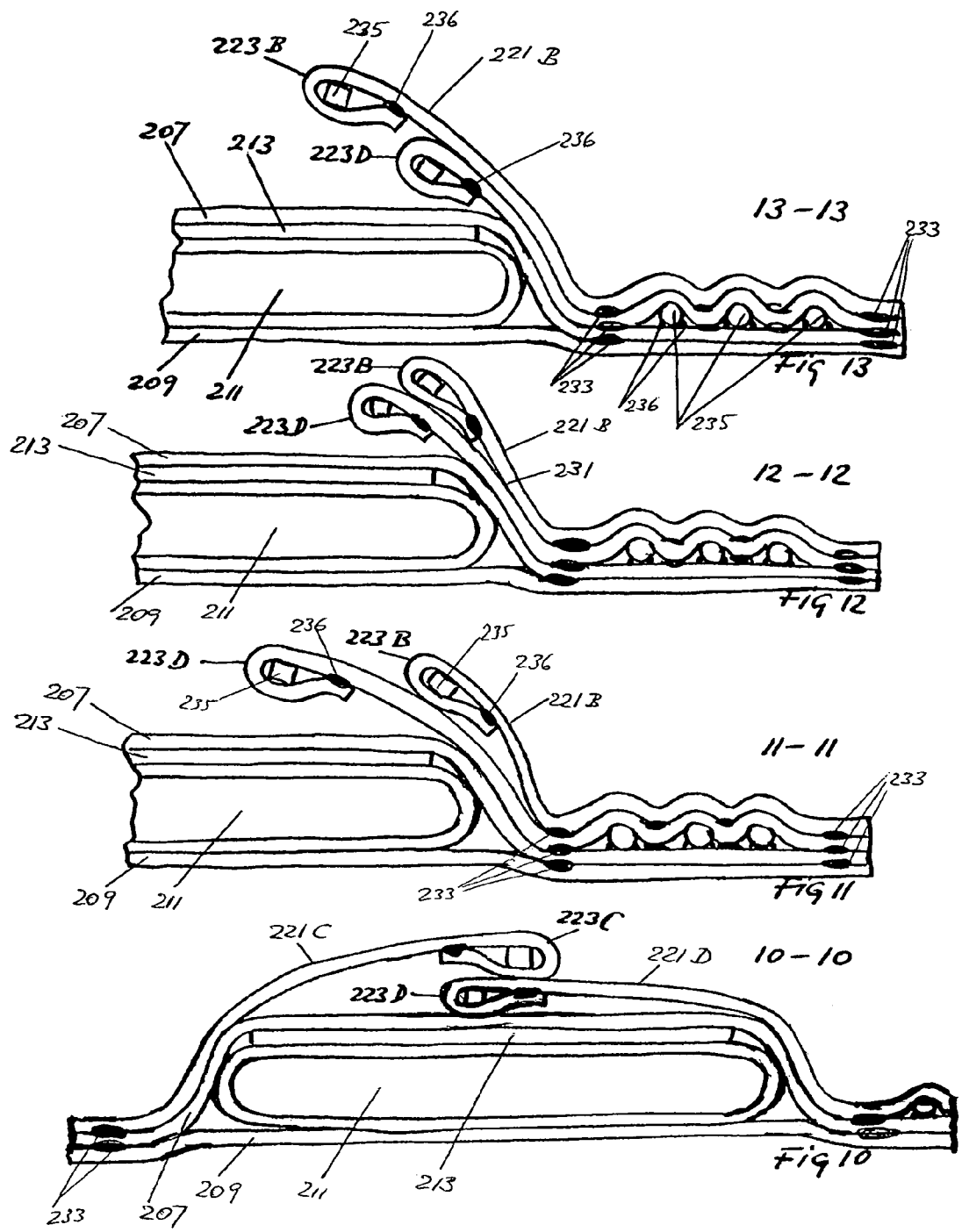

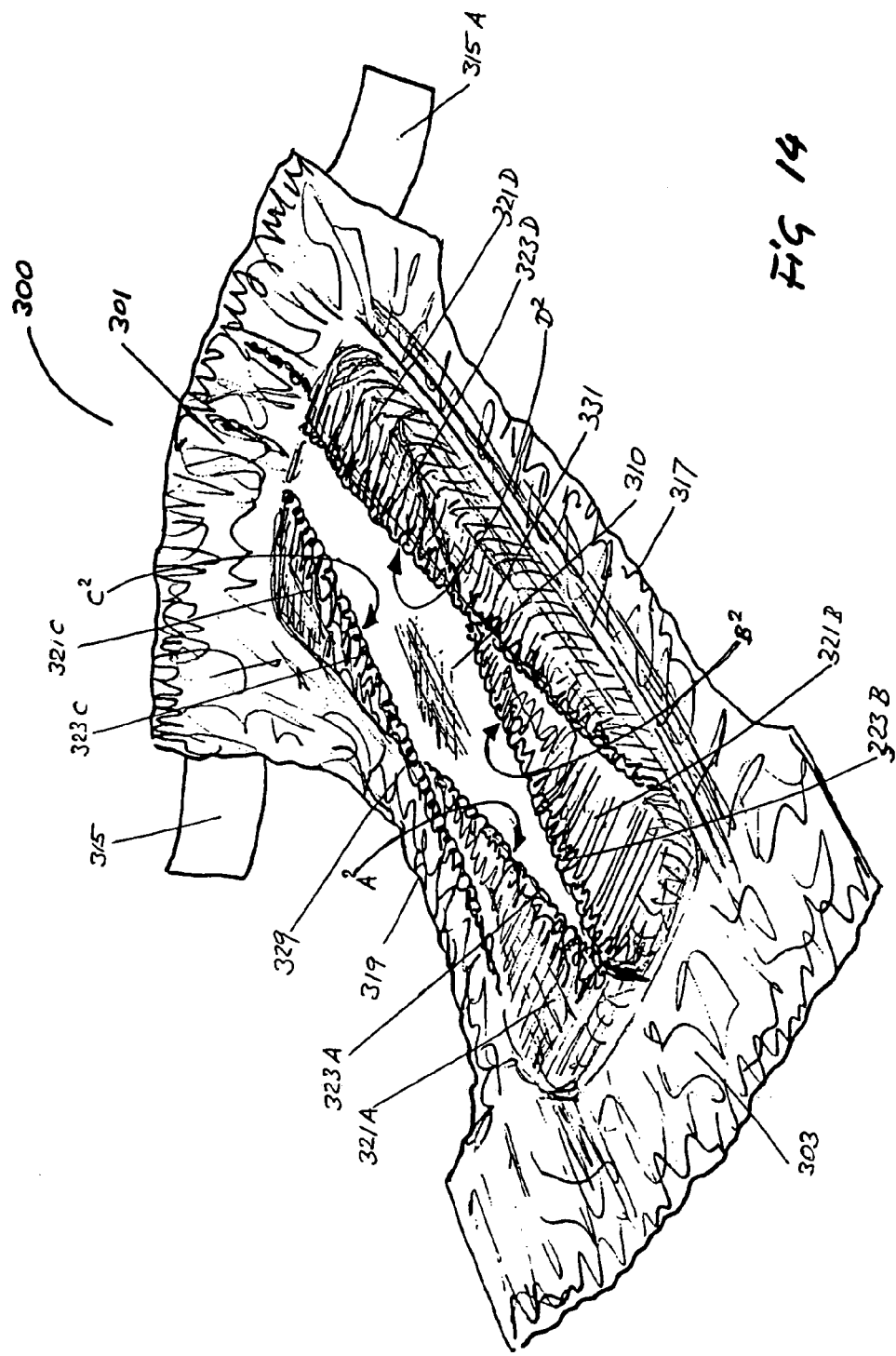

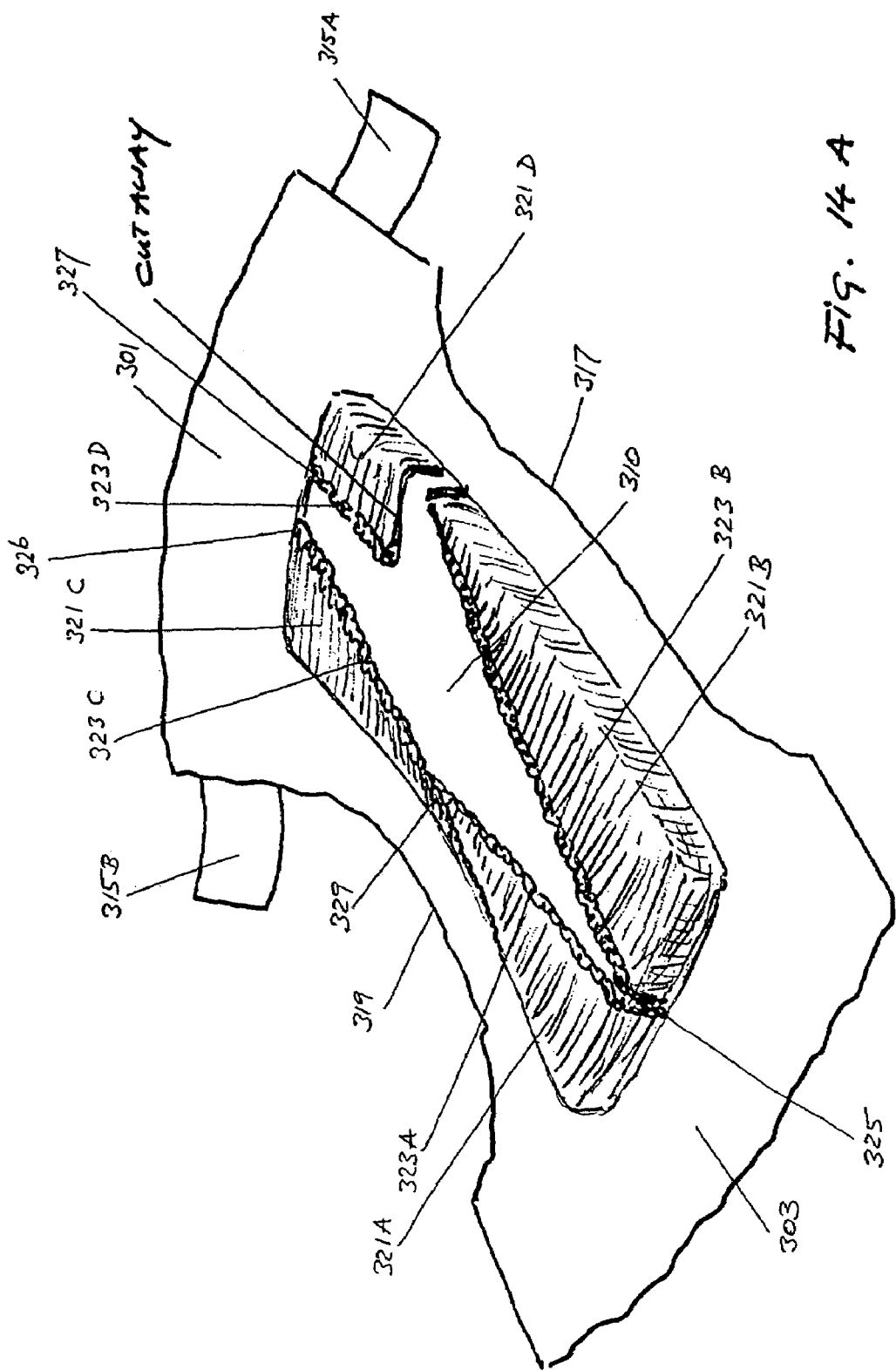

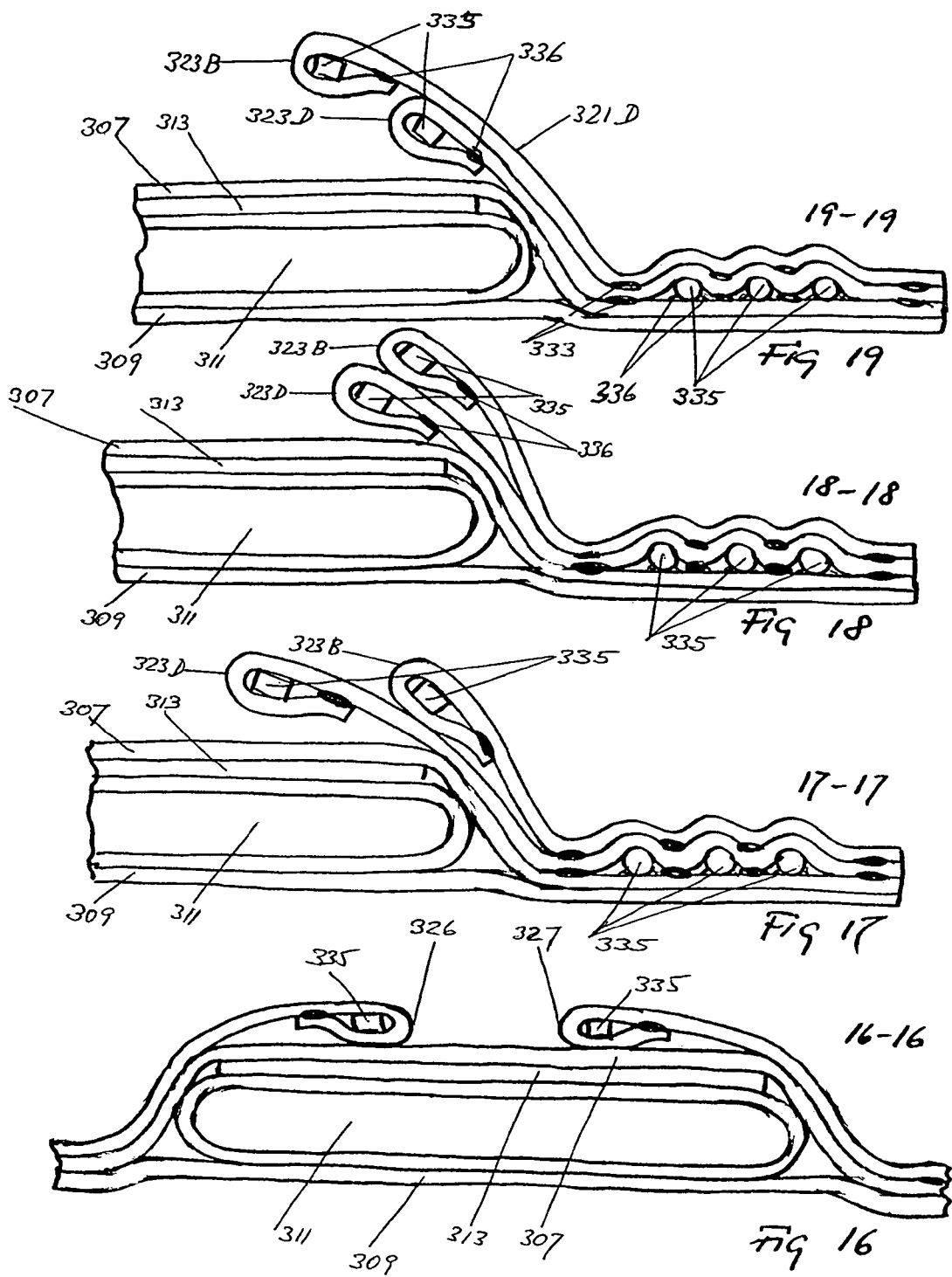

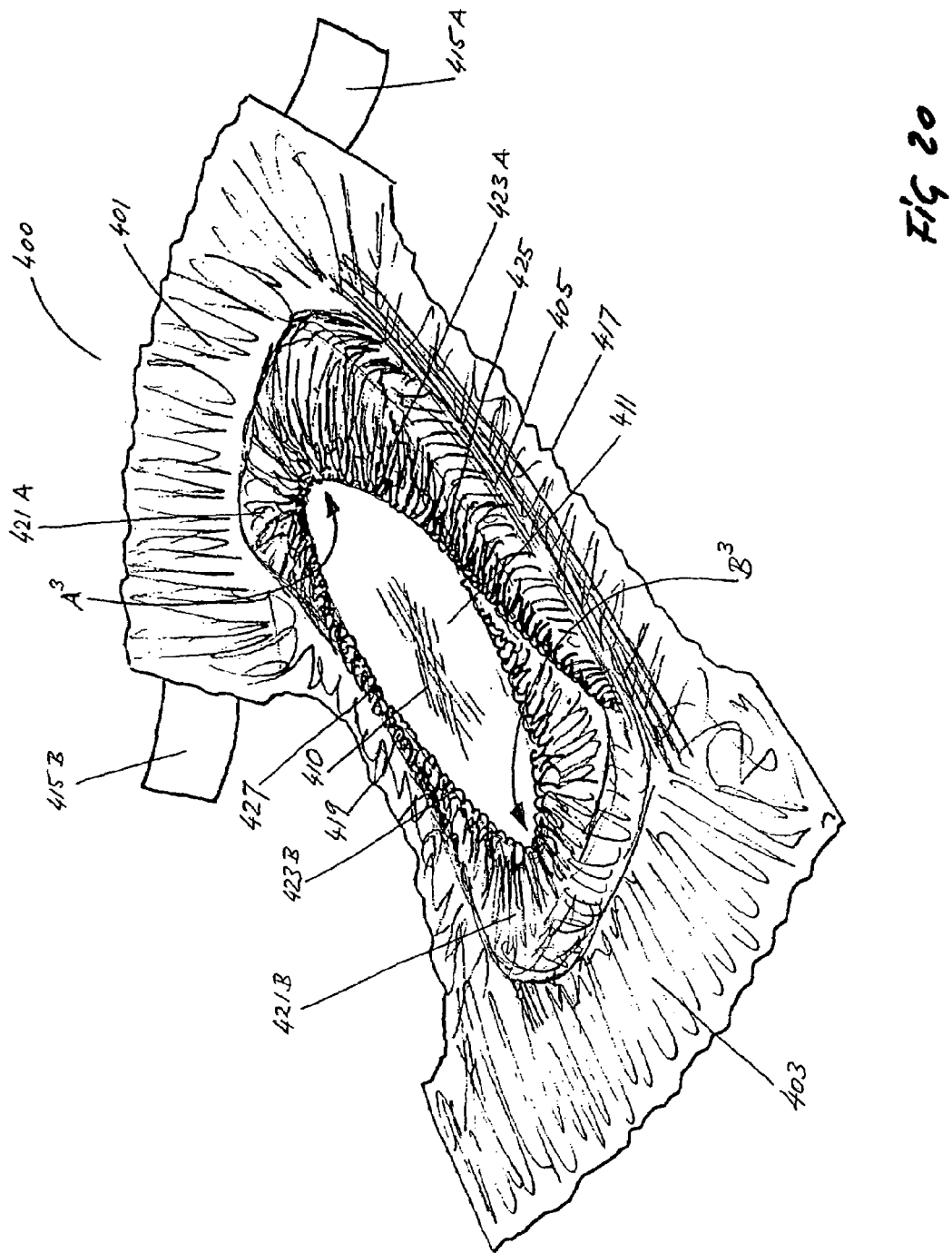

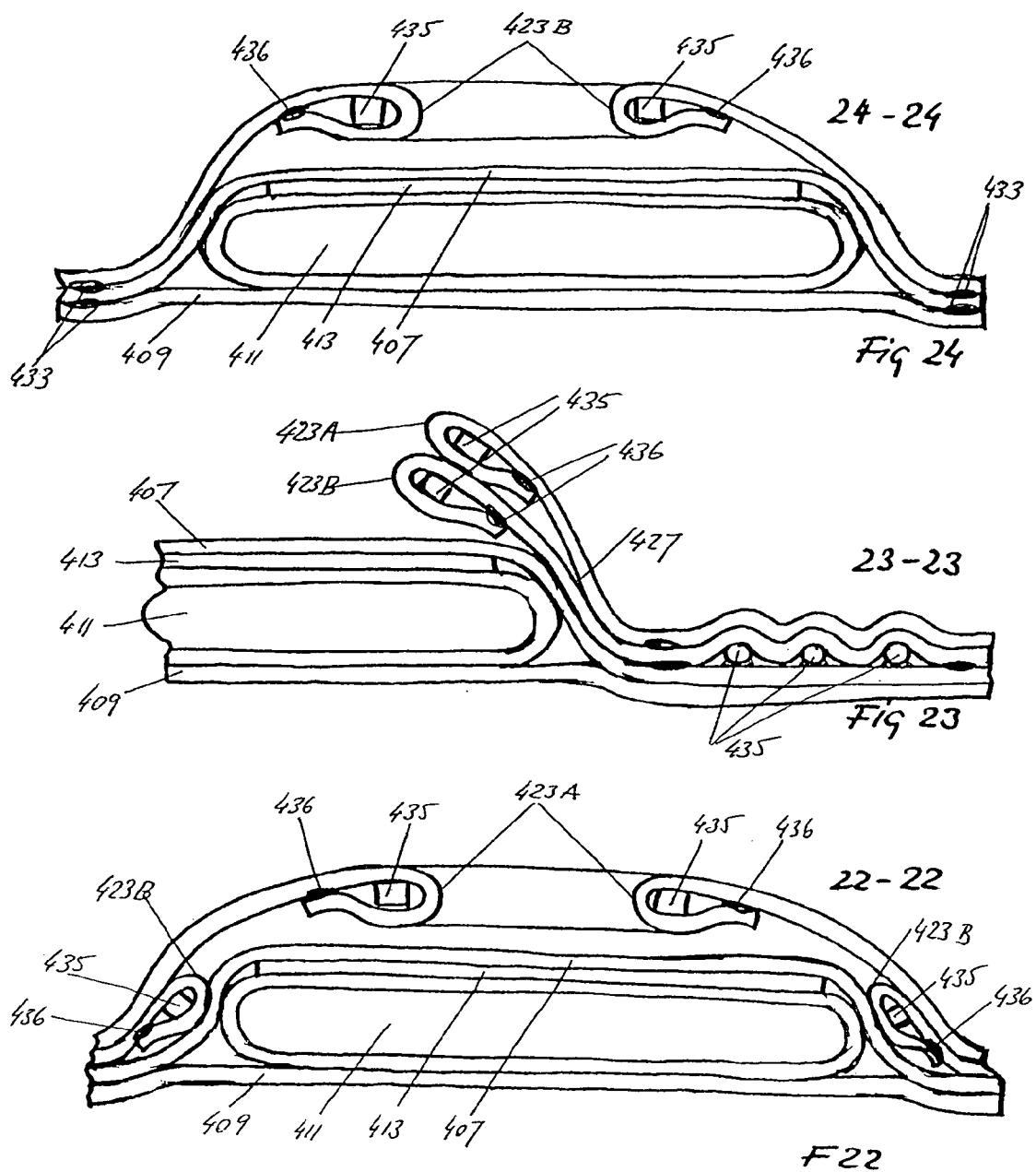

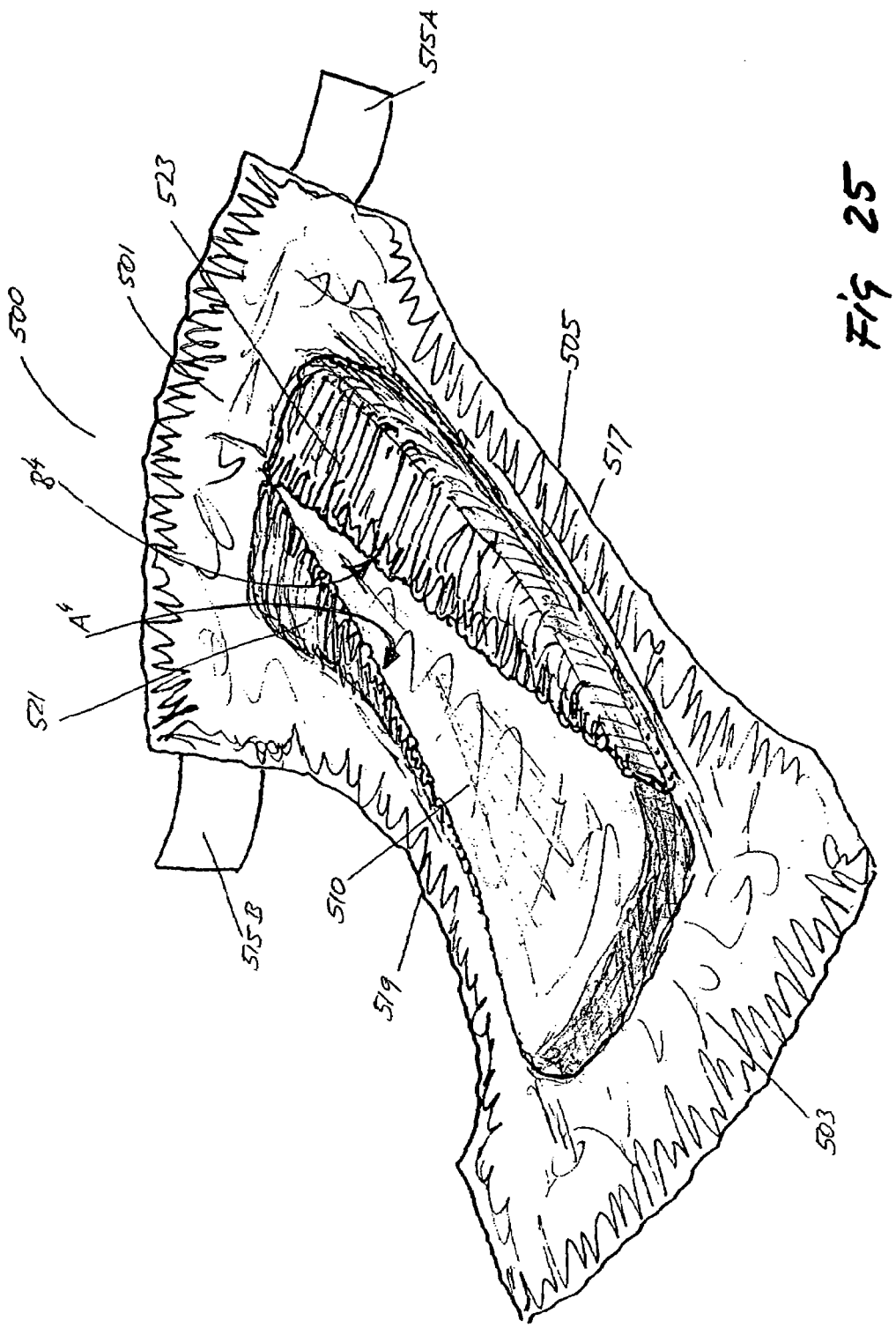

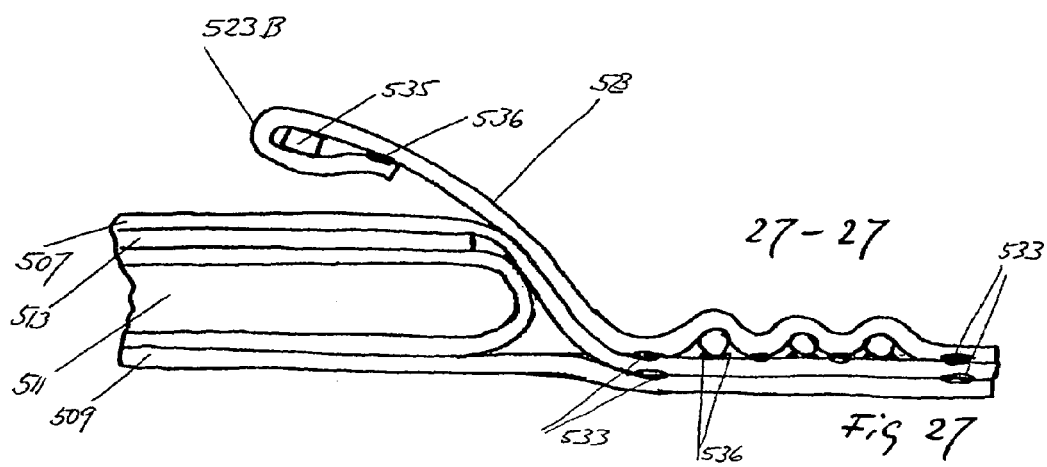
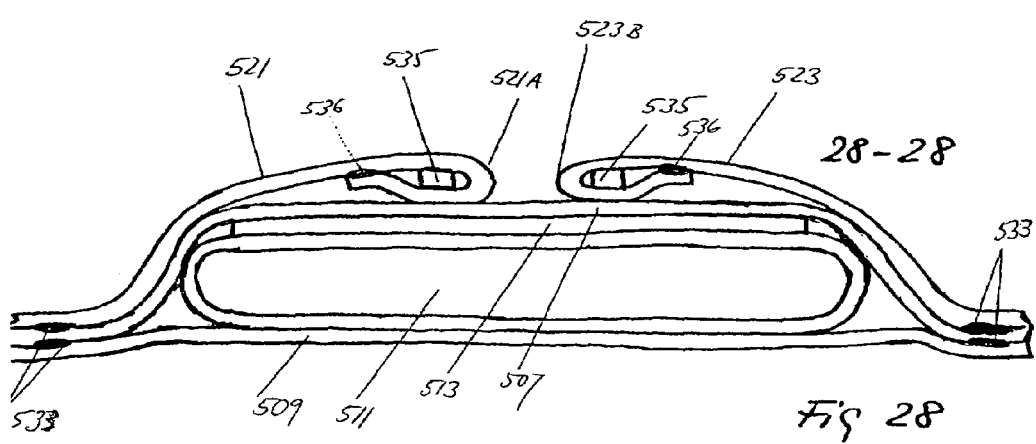

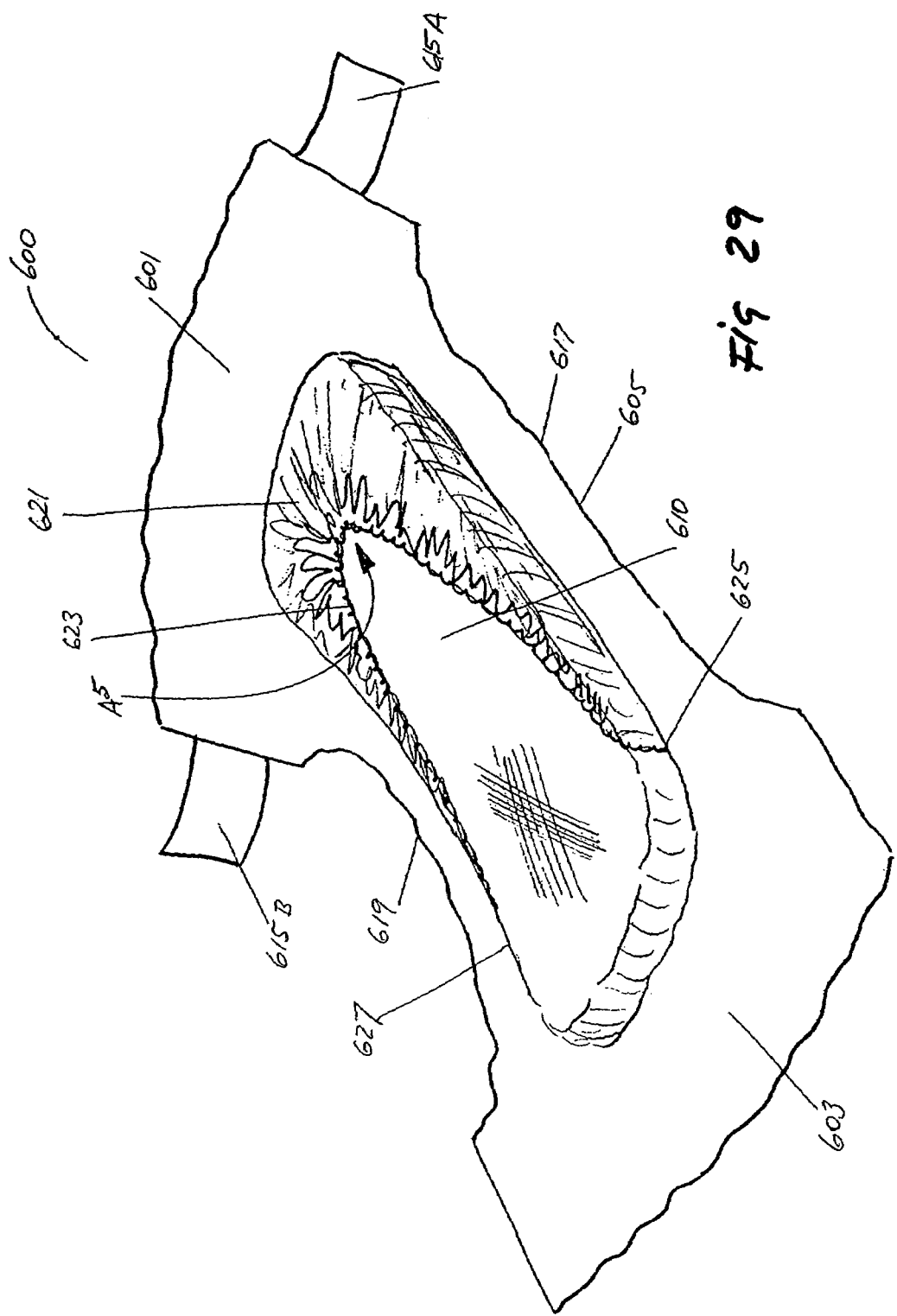

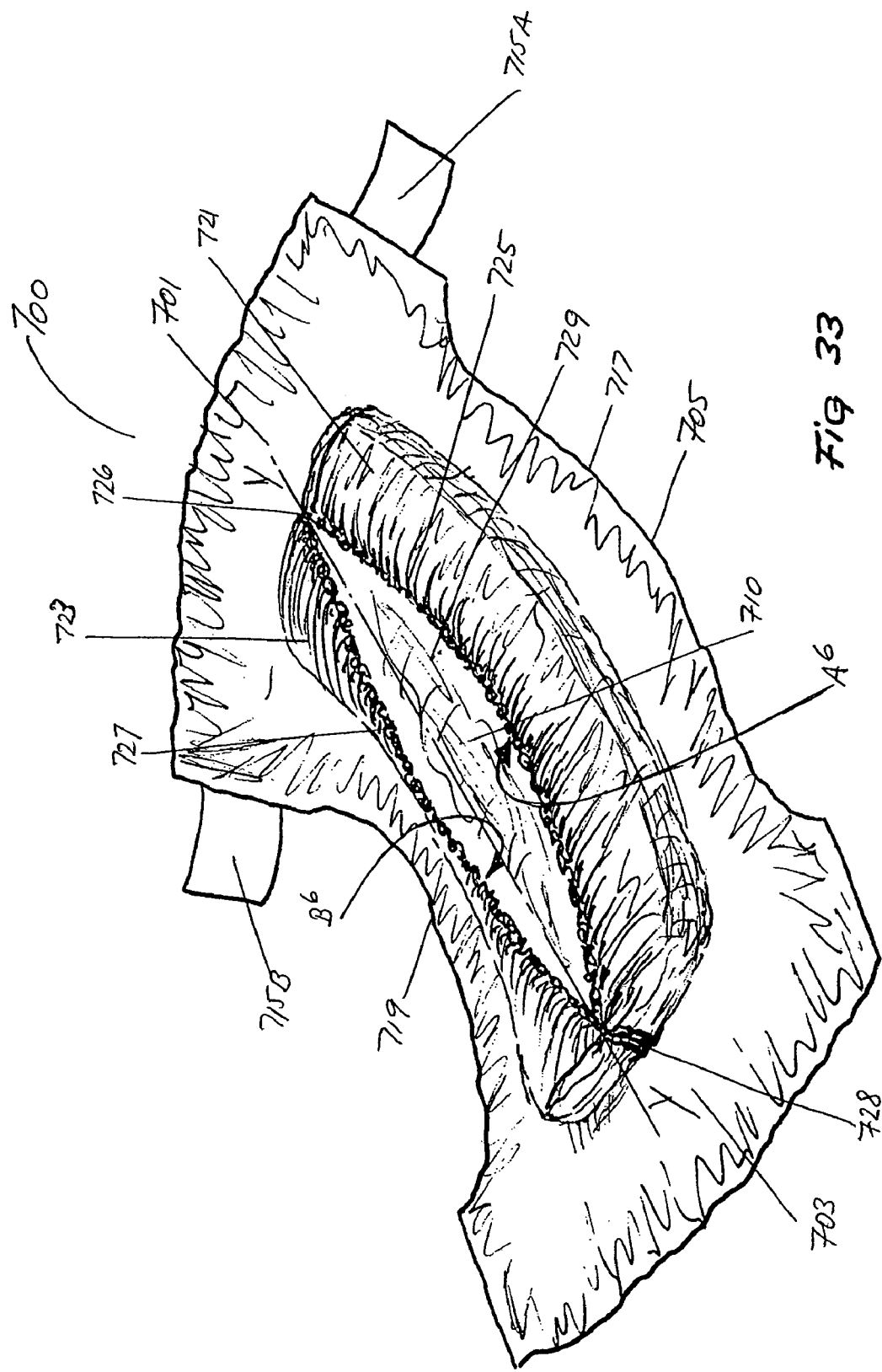

DISPOSABLE ELASTIC ABSORBENT ARTICLE HAVING RETAINING ENCLOSURES

RELATED APPLICATION

This application is a continuation of application No. 09/176,634, filed Oct. 22, 1998, now abandoned, itself a continuation-in-part of pending application Ser. No. 09/097,198, filed Jun. 12, 1998, issued as U.S. Pat. No. 6,413,249.

FIELD OF THE INVENTION

The present invention relates generally to absorbent articles such as disposable diapers, and is more particularly related to infant training pants and adult incontinent underpants, briefs and guards used for absorption and containment of urine and other body exudates. More particularly, the present invention relates to such adult incontinent articles which are easy to wear, securely fit against the body contours for effective prevention against leakage of urine and other body exudates, and which are also easy to remove. In one particular aspect, this invention relates to adults incontinent underpants, briefs and guards having retaining enclosures for preventing body exudates from leaking through the article during use.

BACKGROUND OF THE INVENTION

Disposable absorbent articles such as disposable baby diapers and adult incontinent briefs, underpants, guards and the like articles are widely used in homes and various health care facilities and institutions. Indeed the use of such articles has become a common sanitary practice, and while initially such absorbent articles were used mostly for baby care, more recently their use has been expanded for adults as well. In both instances, the absorbent article must be designed to effectively prevent leakage of urine and other fecal materials, while insuring body fit and comfort.

Present commercially available absorbent articles are generally unitary in structure, pre-shaped and pre-folded, and comprise an absorptive pad having a liquid permeable top sheet facing the wearer's body, a liquid impermeable backsheet on the opposite side, and an absorbent sheet or panel disposed between the top sheet and the back sheet. The absorbent article comprises a front side portion, a crotch portion and a backside portion, and further includes elastic members along the circumference of the waist and around the leg openings. While the heretofore commercially available absorbent articles have been somewhat effective against leakage of body fluids and fecal materials, and have therefore met some degree of acceptability, they have not been entirely satisfactory for their intended applications. In other words, they have not proven to be entirely leak proof, nor have they completely prevented issuance of the body exudates outside the diaper or the underpants. These deficiencies are primarily due to inadequate and loose body fit, which result in leakage of the body fluids and solids through the legs' openings. These problems are even more pronounced in case of adults because of their diverse body shapes and varying contours. Another disadvantage of the commercially available absorbent articles such as diapers, incontinent briefs and the like, is associated with the ability of opening and removing the soiled article without soiling the wearer's legs or body.

There is a plethora of patents which disclose the different attempts made by the prior art workers over the years to eliminate, or at least minimize, the shortcomings of the present commercially available absorbent articles.

U.S. Pat. No. 4,795,454 describes an absorbent article provided with an elastically contractible gasketing cuff formed by a gasketing flap and a flap elastic member and a barrier cuff having a flap portion and a channel portion. A seal means for adjoining the proximal edge to the gasketing flap is positioned along the proximal edge so as provide a leak resistant seal along the proximal edge.

U.S. Pat. No. 5,599,338 describes a disposable diaper provided with a first and second flap formed from or attached to the bodyside liner. The flaps may be folded inwardly and the respective ends thereof may be bonded to the bodyside liner so that edges of flaps are directed toward a centerline of the garment.

PCT WO96/17570//EP 796066 describes a disposable diaper having a waist pocket cuff which has first and second portions separable along a releasable seam. The releasable seam can be formed by overlapping portions of the first and second portions of the pocket cuff. In one embodiment the releasable seam includes a mechanical fastener for securing together the first and second portions of the pocket cuff.

EP 0 707 466 describes an absorbent sanitary article which comprises an absorbent pad between a backing sheet and a covering sheet. The covering sheet comprises a central opening which extends above the absorbent pad and sets of elastic means are fixed to the covering sheet along the longitudinal edges of the central opening. The article is characterized in that it comprises a set of two hydrophobic flaps which are symmetrical with respect to the longitudinal axis.

Notwithstanding attempts by the prior art workers to provide absorbent articles with improved body fit and protection against leakage of body exudates, nevertheless additional improvements are needed for providing a more suitable absorbent article.

The foregoing patents by no means constitute an exhaustive list of the patents which reflect the efforts of the prior art workers in this field, but are merely illustrative for background purposes. As it can be appreciated, however, notwithstanding attempts by others to provide satisfactory absorbent articles for infants as well as for incontinent adults, there is still a need for providing improved articles commercially, which are highly effective in preventing leakage of urine and other body exudates, and which are comfortable to wear and conformably fit the body contours so as to insure against such leakage and prevent soiling the wearer's body as well as the person who applies the garment to the wearer.

Accordingly, it is an object of the present invention to provide a disposable absorbent article such as baby diapers, adult incontinent underpants, briefs, guards and the like articles, which overcome the deficiencies and shortcomings of the prior art absorbent articles, including the present commercially available products used for this purpose.

It is another object of this invention to provide a disposable absorbent articles which, due to its unique construction, provide improved fit to the body and prevent leakage of urine and other body exudates through the leg openings by providing the article with exudate-retaining enclosures.

It is also an object of this invention to provide such disposable absorbent articles which have tensionable elastic elements which insure body fit and conformal movements in response to the body shape and contours, and provides for examination of the condition of the article.

The foregoing and other objects and features of the present invention will be more fully comprehended and appreciated from the ensuing detailed description and the figures in the drawing which form parts of the application.

SUMMARY OF THE INVENTION

In accordance with this invention an integral disposable elasticized absorbent article is provided having a front waist portion, a back waist portion, a crotch portion, a pair of spaced apart leg openings, an absorbent core member, and means for fastening the absorbent body snugly to the body of the wearer. In one embodiment of the invention the absorbent article has an elasticized barrier layer securely fixed at the longitudinal and lateral sides of the body and having inner elasticized edges. The elasticized barrier layer overlies a portion of the absorbent core and forms a retaining enclosure between said barrier layer and said portion of the absorbent core.

In different embodiments of the invention the elasticized barrier layer comprises two or more segments which form retaining enclosures with the underlying portions of the core member.

BRIEF DESCRIPTION OF THE DRAWINGS

In the drawings, wherein like reference numerals designate like parts:

FIG. 1A is a cutaway view of the absorbent article shown in FIG. 1 with a portion removed.

FIG. 2 is a perspective view of the absorbent panel of the absorbent article shown in FIG. 1, in bowed position;

FIG. 3 is a sectional view taken along the line 3—3 in FIG. 2;

FIG. 5 is a sectional view taken along the line 5—5 in FIG. 4;

FIG. 6 is a sectional view taken along the line 6—6 in FIG. 4;

FIG. 7 is a sectional view taken along the line 7—7 in FIG. 4;

FIG. 8 is a perspective view of an absorbent article according to another embodiment of the invention;

FIG. 10 is a sectional view taken along the line 10—10 in FIG. 9;

FIG. 11 is a sectional view taken along the line 11—11 in FIG. 9;

FIG. 12 is a sectional view taken along the line 12—12 I FIG. 9;

FIG. 13 is a sectional view taken along the line 13—13 in FIG. 13;

FIG. 14 is a perspective view of an absorbent article according to yet another embodiment of the invention;

FIG. 14A is a cutaway view of the absorbent article shown in FIG. 14 with a portion removed;

FIG. 16 is a sectional view taken along the line 16—16 in FIG. 15;

FIG. 17 is a sectional view taken along the line 17—17 in FIG. 15;

FIG. 18 is a sectional view taken along the line 18—18 in FIG. 15;

FIG. 19 is a sectional view taken along the line 19—19 in FIG. 15;

FIG. 20 is a perspective view of an absorbent article made according to another embodiment of the invention;

FIG. 22 is a sectional view taken along the line 22—22 in FIG. 21;

FIG. 23 is a sectional view taken along the line 23—23 in FIG. 21;

FIG. 24 is a sectional view taken along the line 24—24 in FIG. 21;

FIG. 25 is a perspective view of an absorbent article according to another embodiment of this invention;

FIG. 27 is a sectional view taken along the line 27—27 in FIG. 26;

FIG. 28 is a sectional view taken along the line 28—28 in FIG. 26;

FIG. 29 is a perspective view of an absorbent article made according to still another embodiment of the invention;

FIG. 33 is a perspective view of a further embodiment of the present invention;

DETAILED DESCRIPTION OF THE INVENTION

Figure 1:
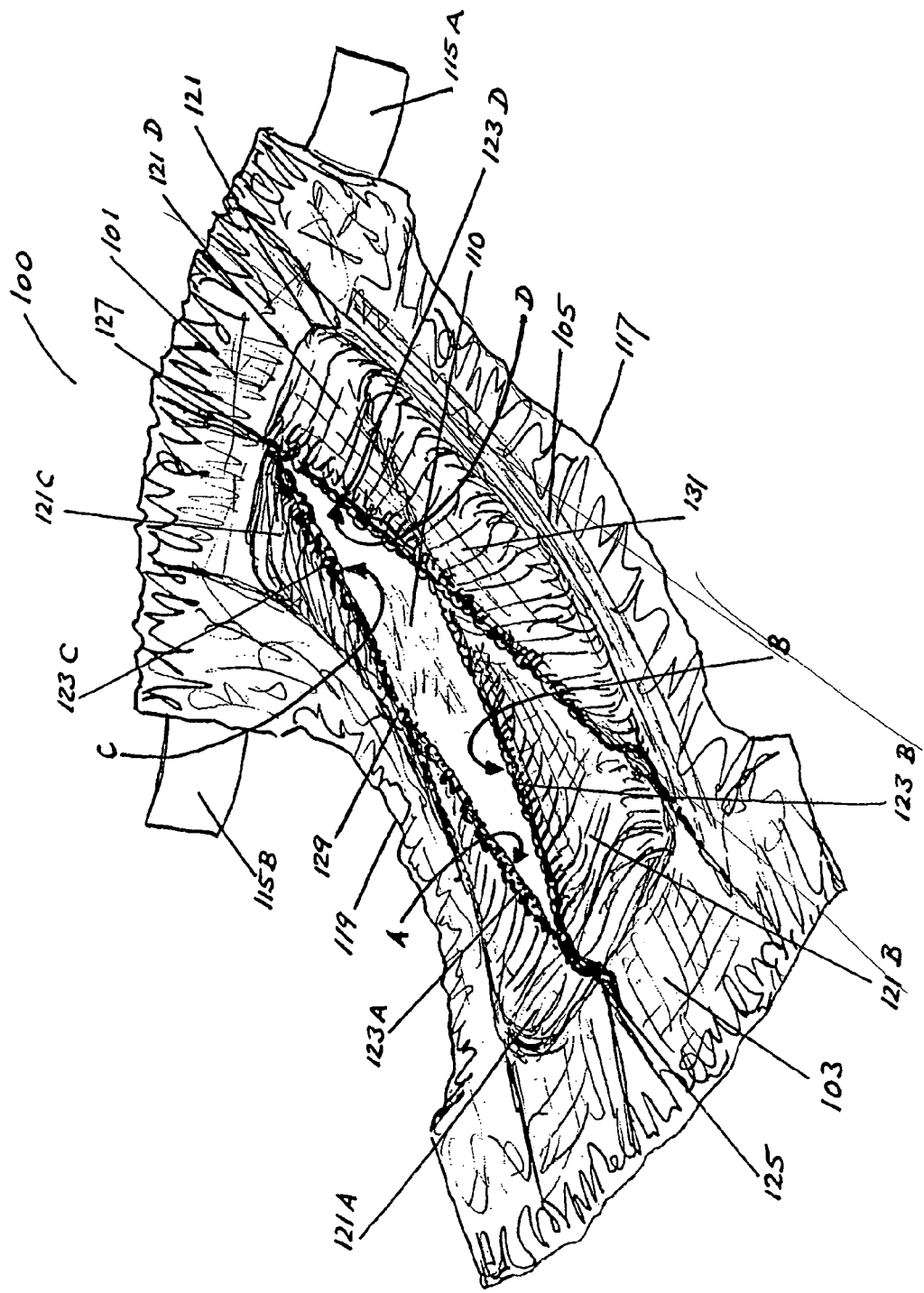
FIG. 1 is a perspective view of an absorbent article, in stretched position, according to one embodiment of the invention.
Figure 4:
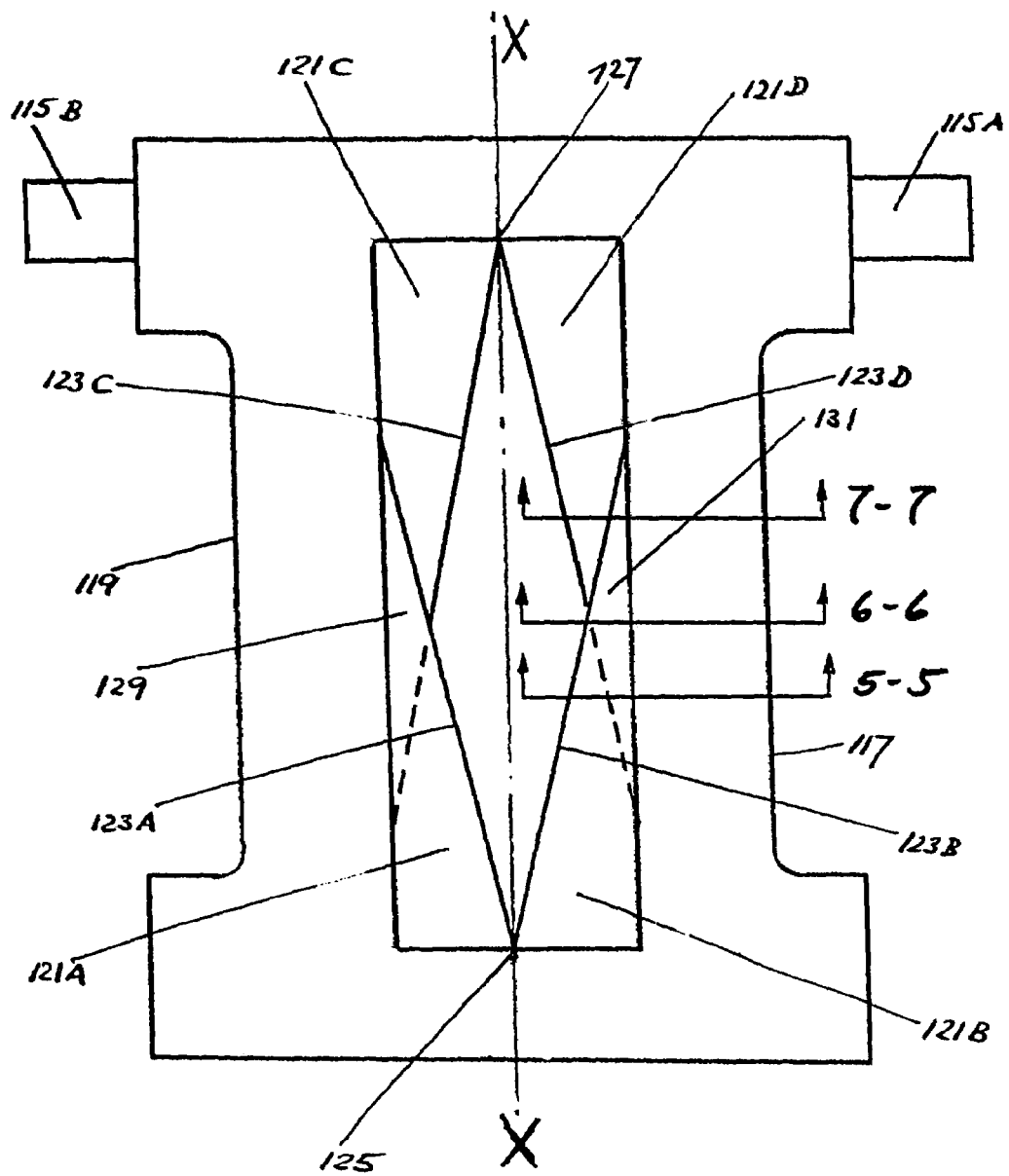
FIG. 4 is a stretched plan view of the absorbent article shown in FIG. 1.
Figure 8A:
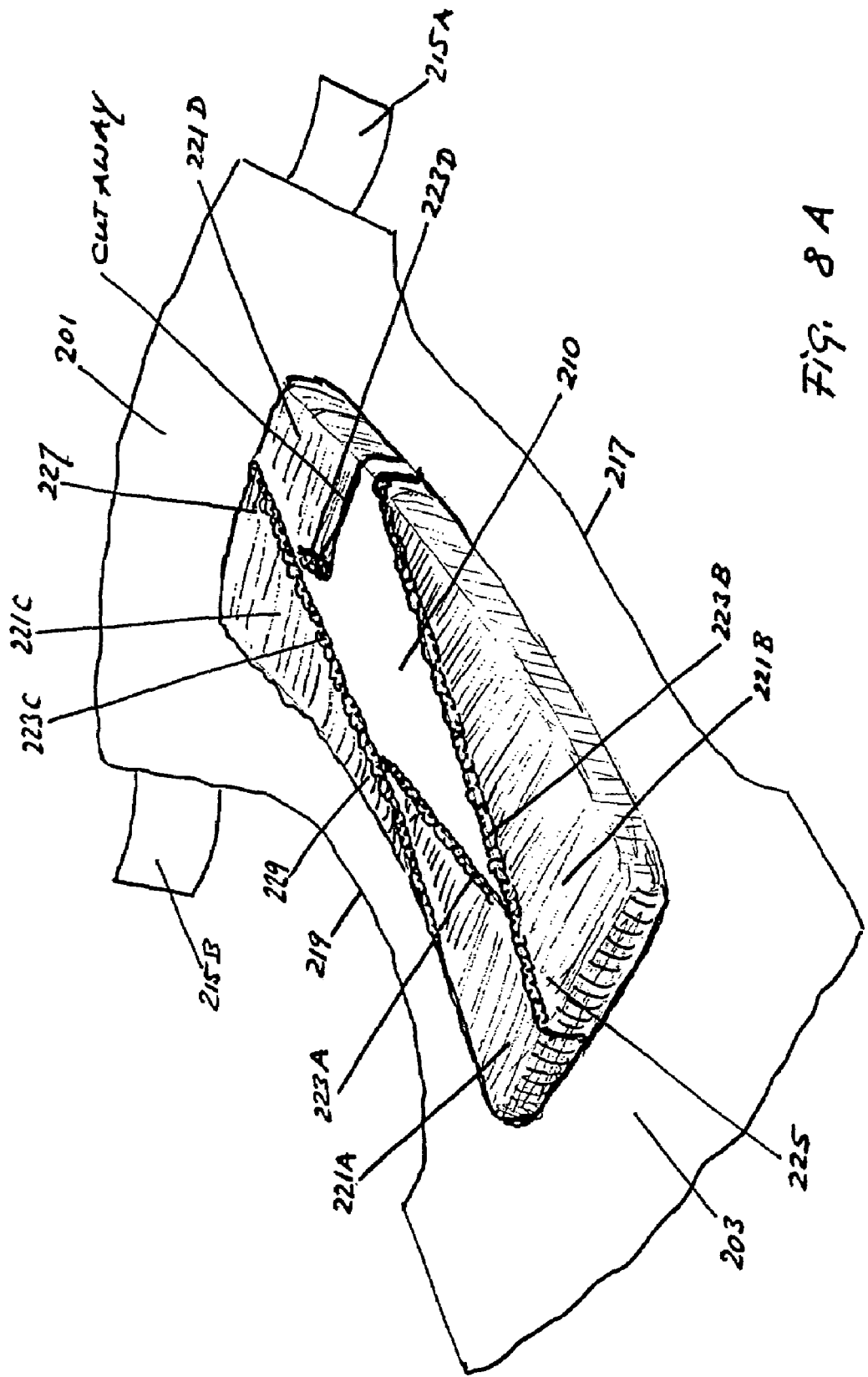
FIG. 8A is a cutaway view of the absorbent article shown in FIG. 8 with a portion removed.
Figure 9:
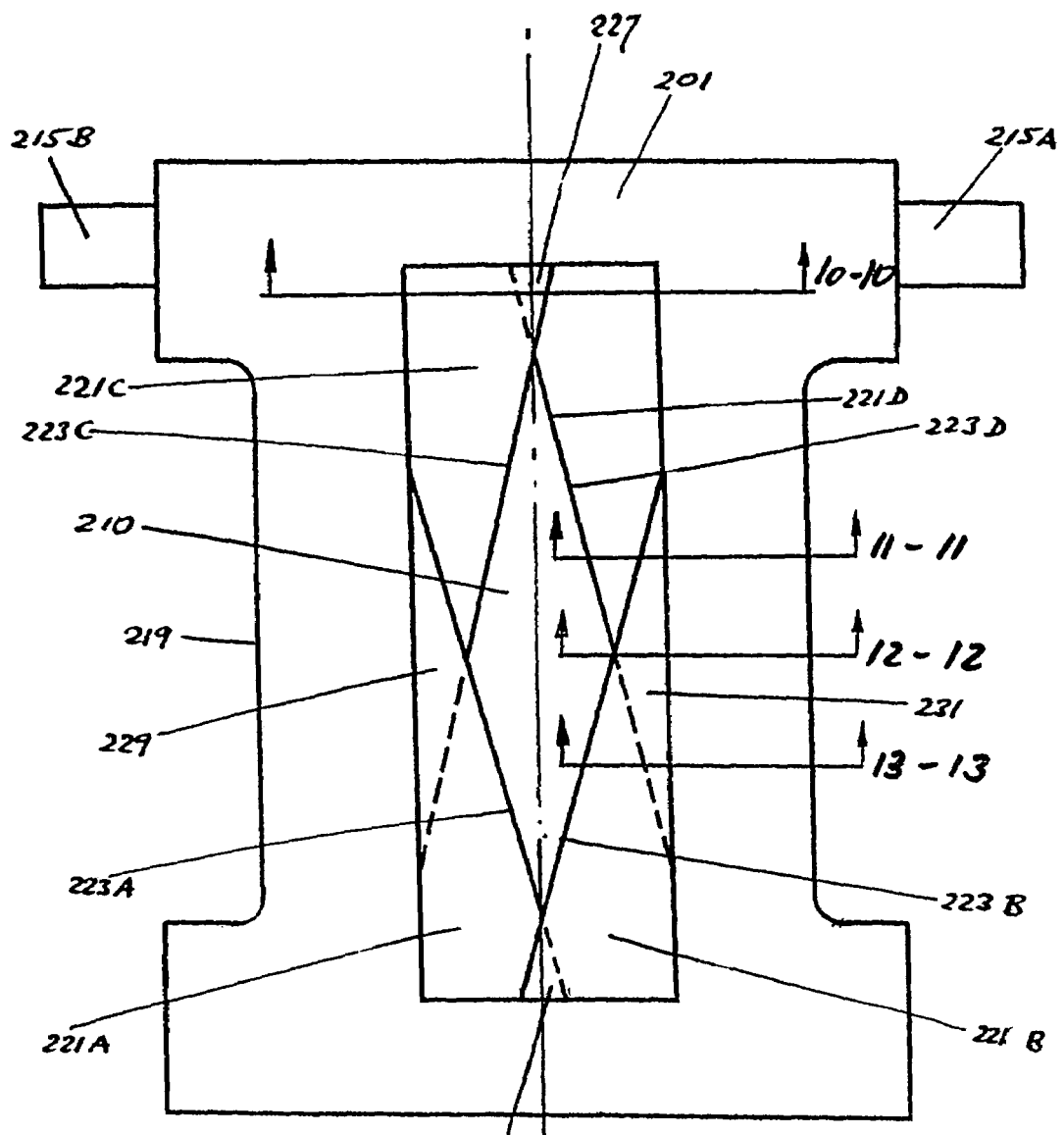
FIG. 9 is a stretched plan view of the absorbent article shown in FIG. 8.
Figure 15:
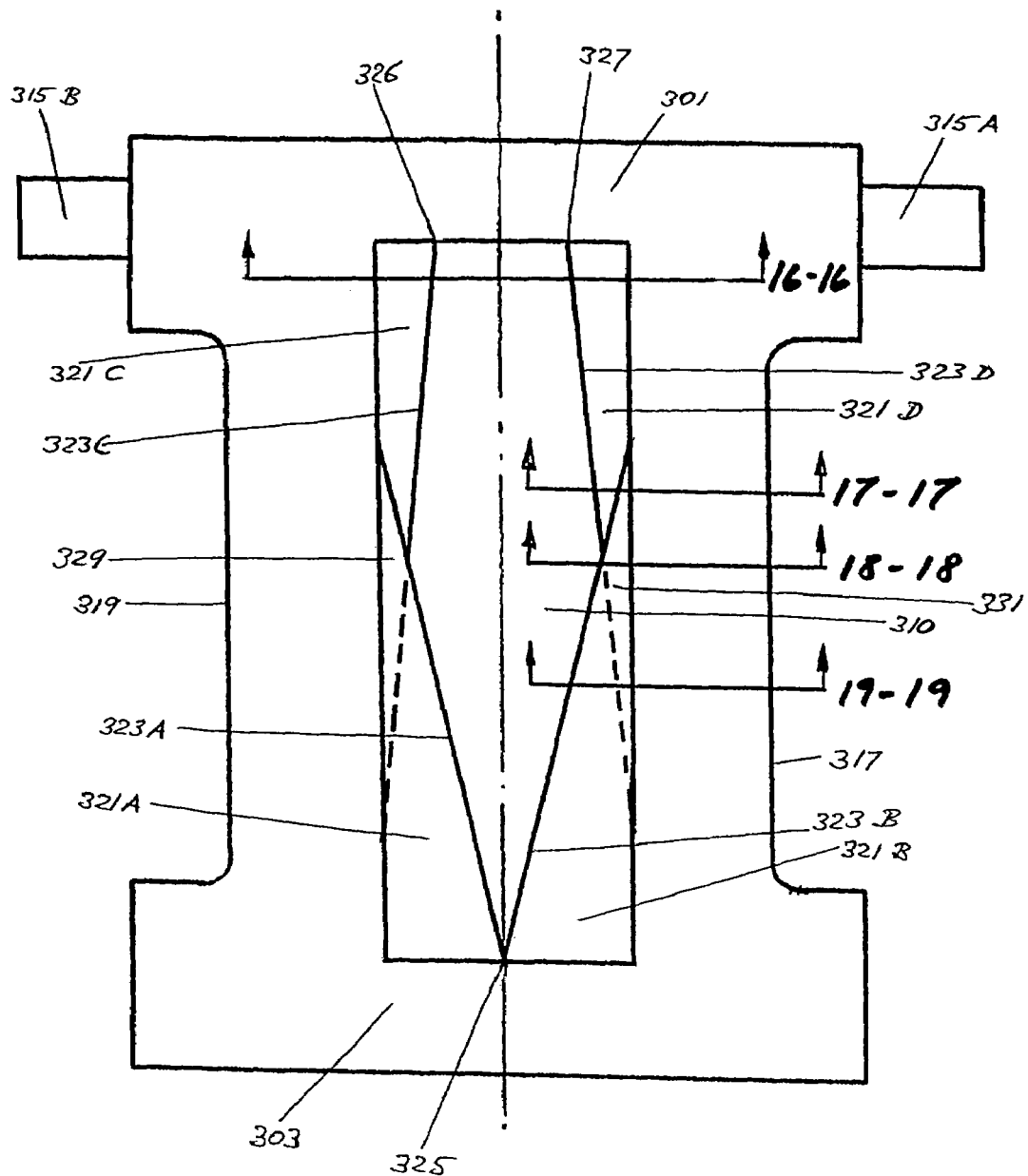
FIG. 15 is a stretched plan view of the absorbent article shown in FIG. 14.
Figure 21:
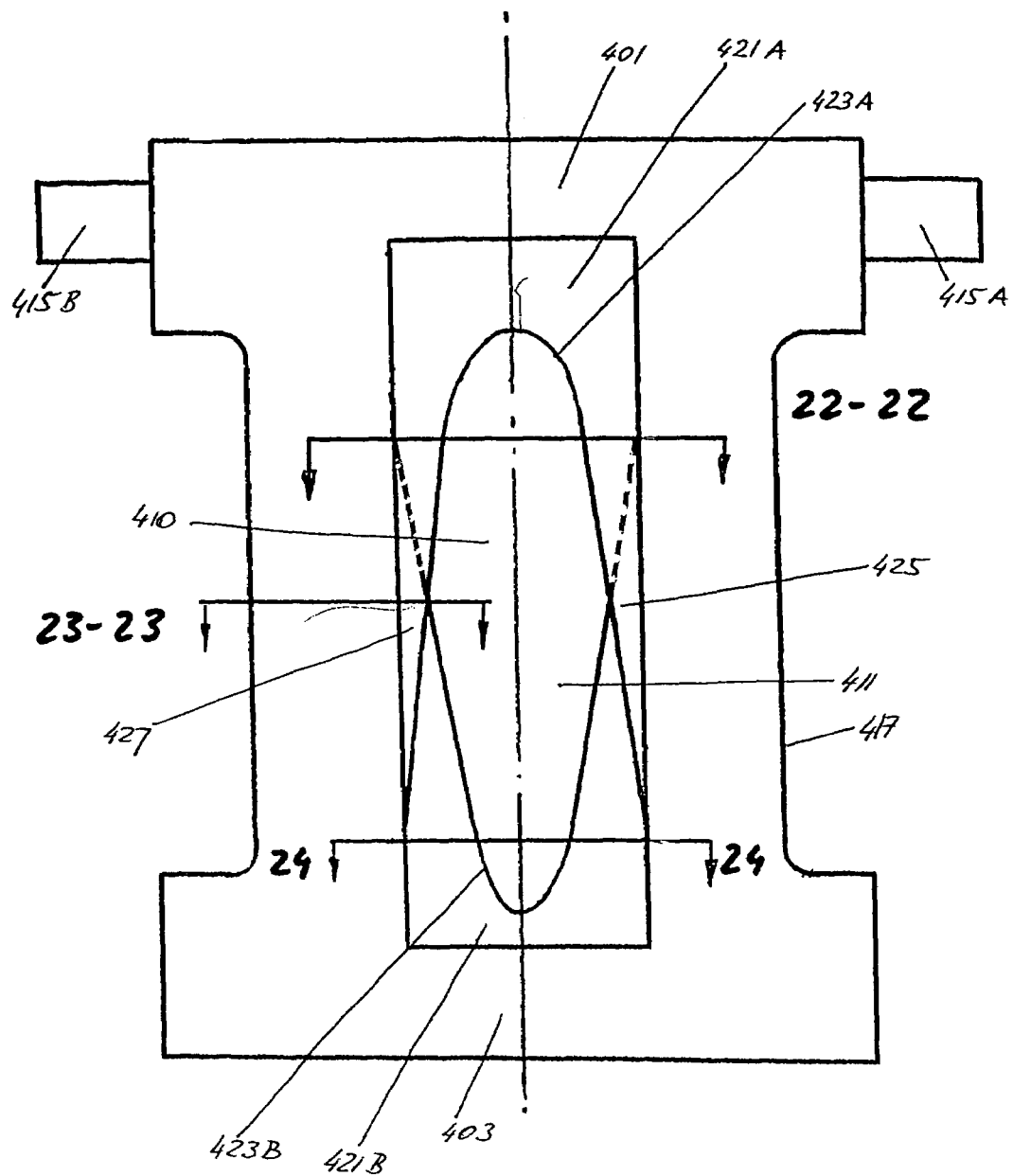
FIG. 21 is a stretched plan view of the absorbent article shown in FIG. 20.
Figure 26:
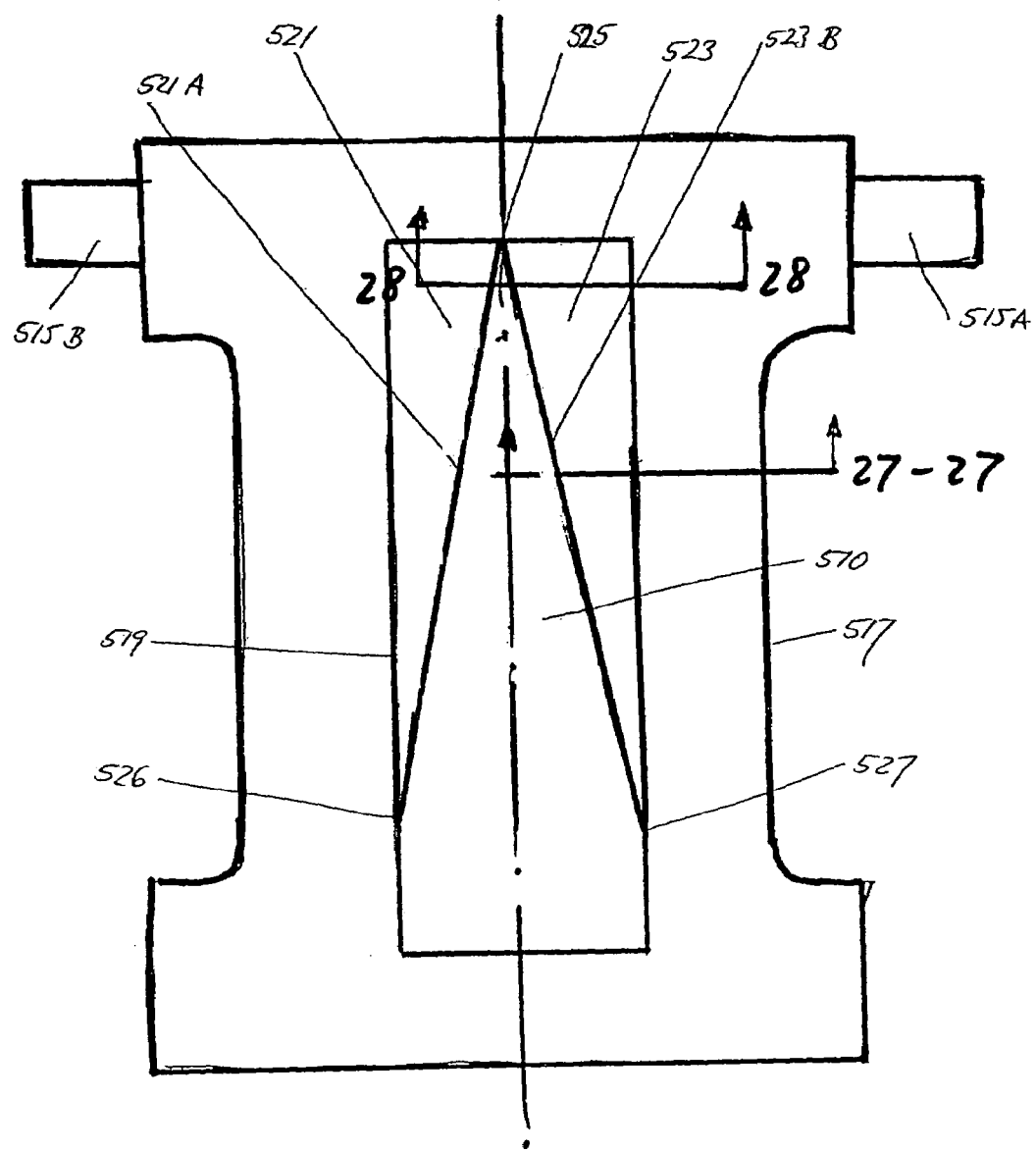
FIG. 26 is a stretched plan view of the absorbent article shown in FIG. 25.
Figure 30:
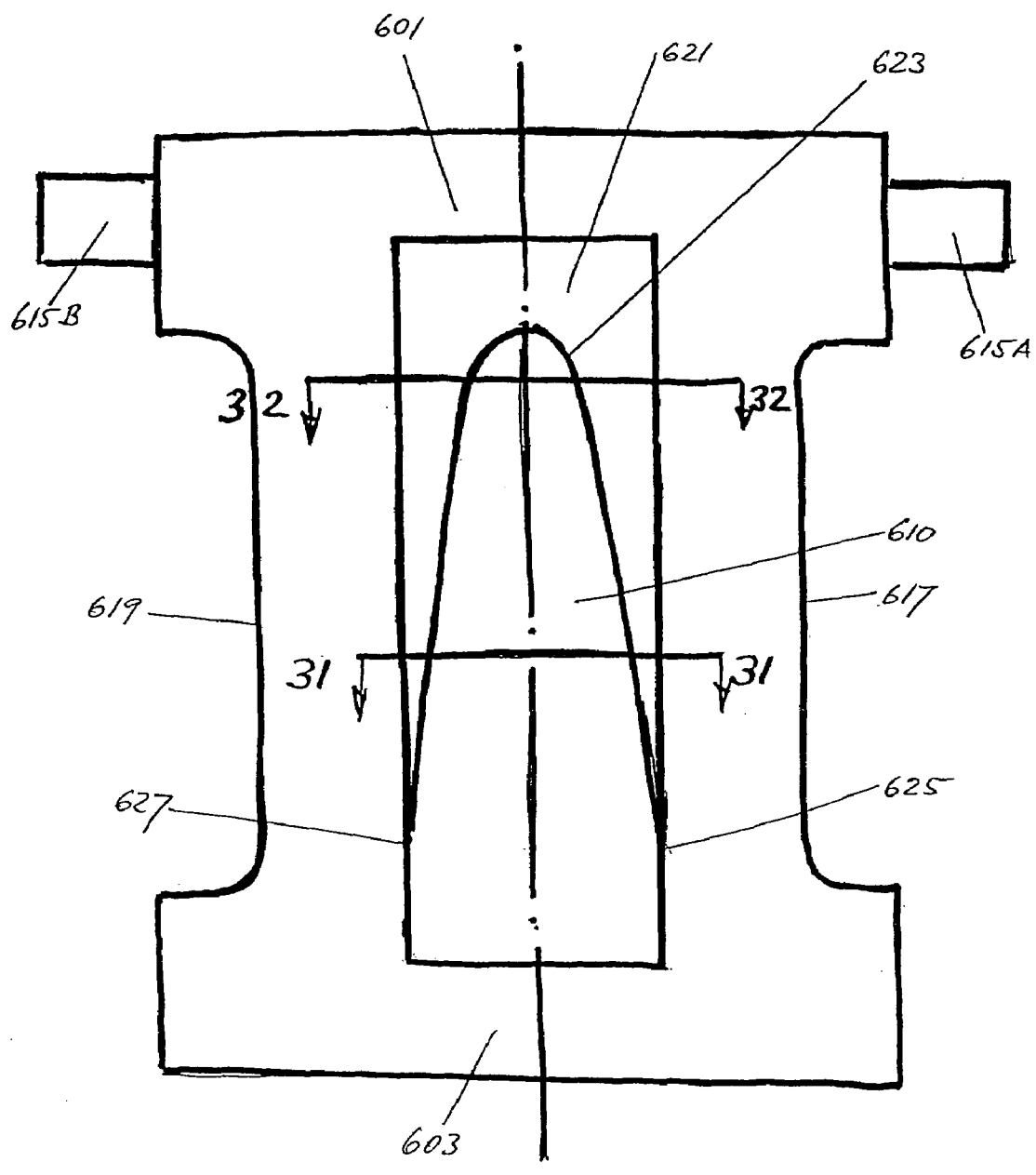
FIG. 30 is a stretched plan view of the absorbent article shown in FIG. 29.
Figure 32:
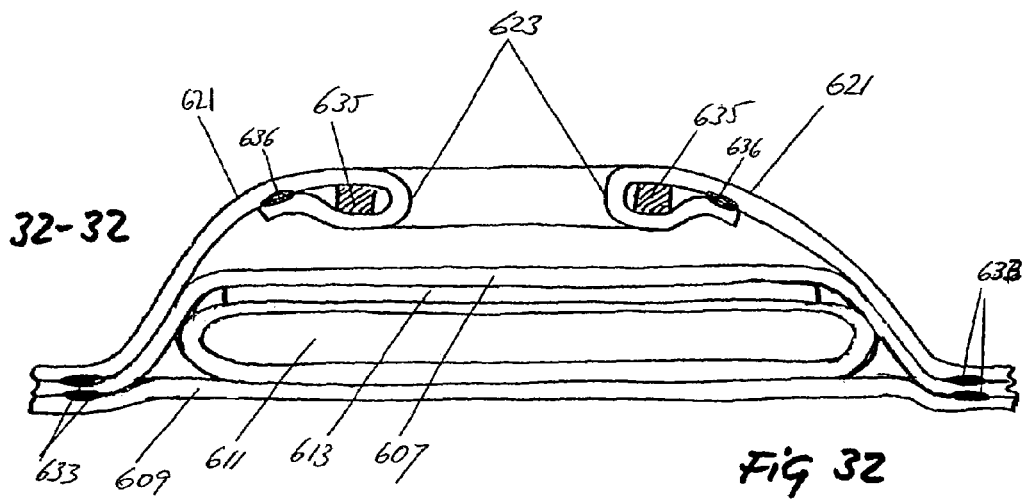
FIG. 32 is a sectional view taken along the line 32—32 in FIG. 30.
Figure 31:
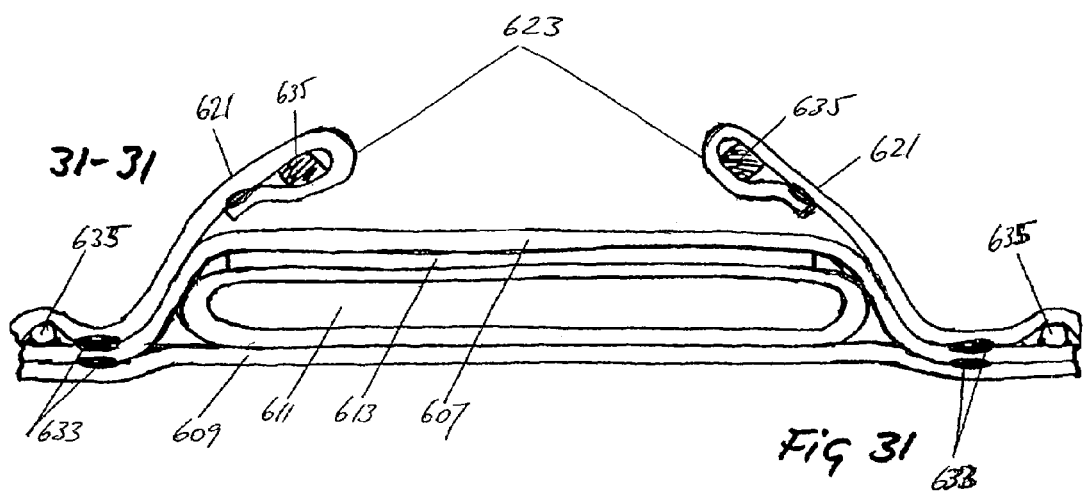
FIG. 31 is a sectional view taken along the line 31—31 in FIG. 30.
Figure 34:
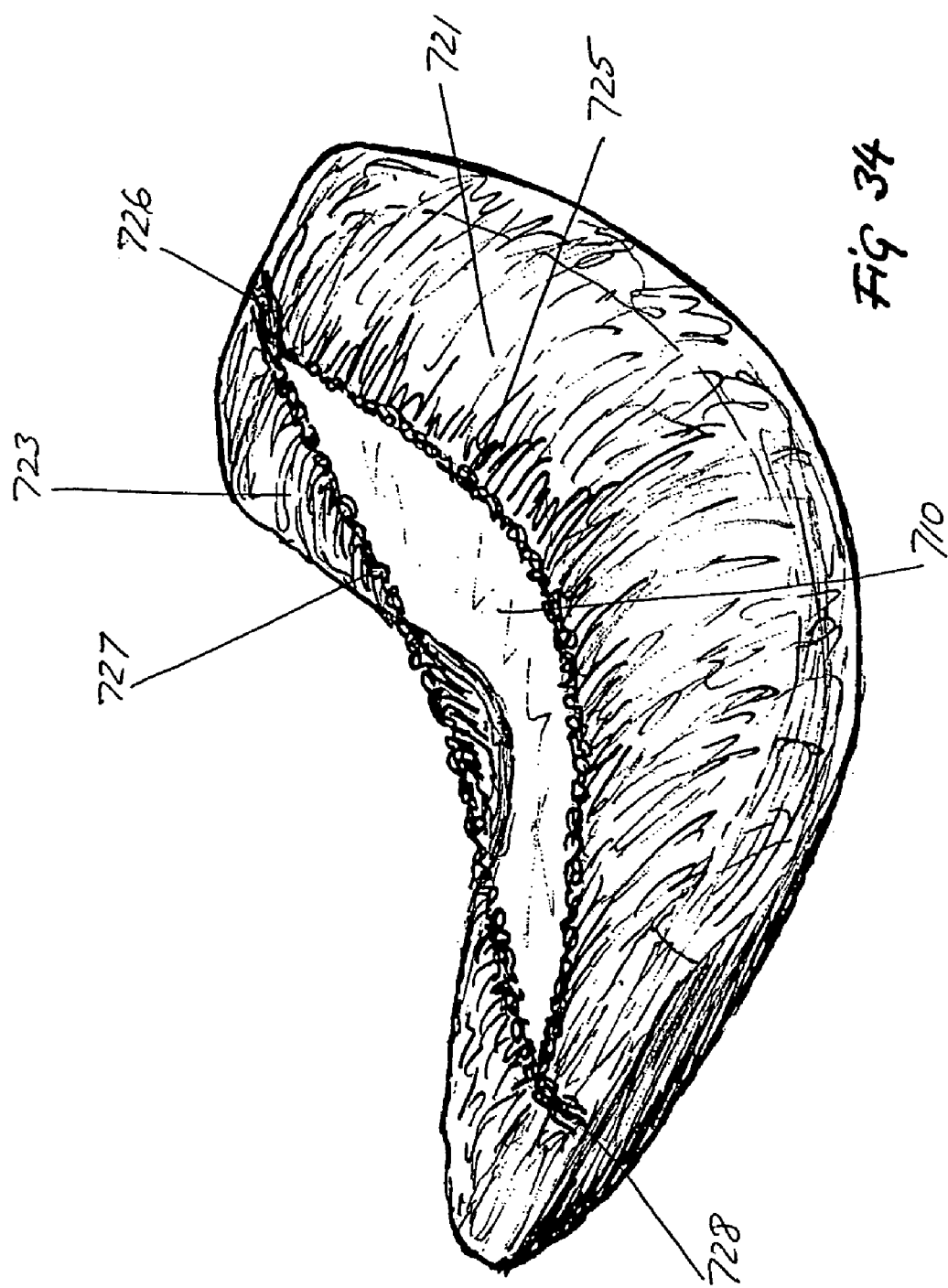
FIG. 34 is a perspective view of the absorbent pad of the absorbent article shown in FIG. 33, in bowed position.
Figure 35:
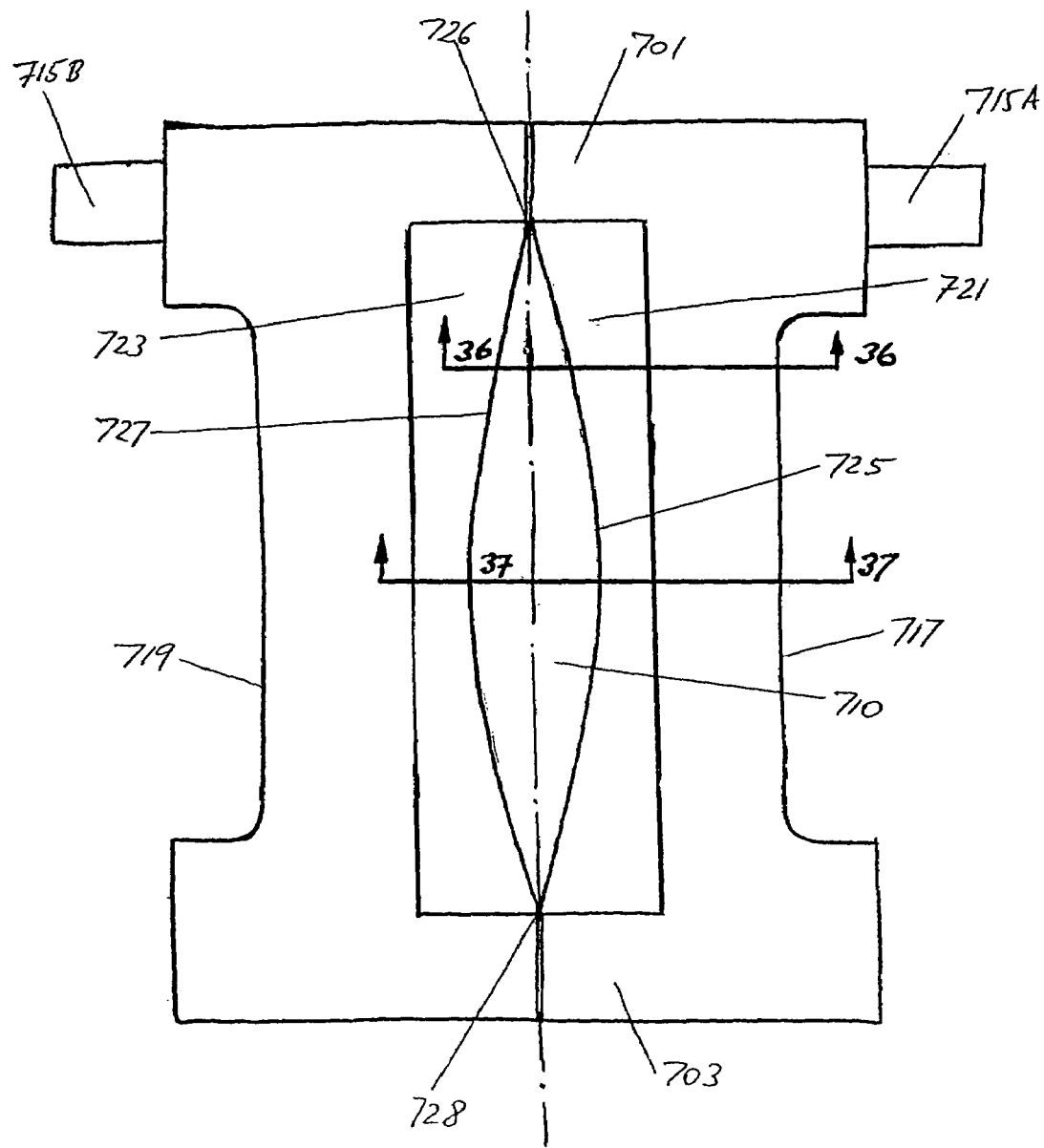
FIG. 35 is a stretched plan view of the embodiment shown in FIG. 33.
Figure 36:
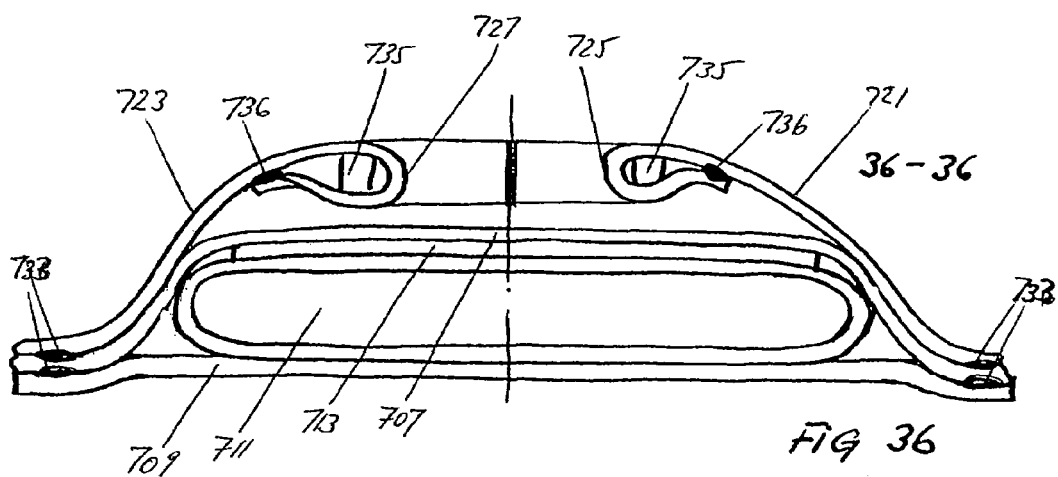
FIG. 36 is a sectional view taken along the line 36—36 of FIG. 35.
Figure 37:
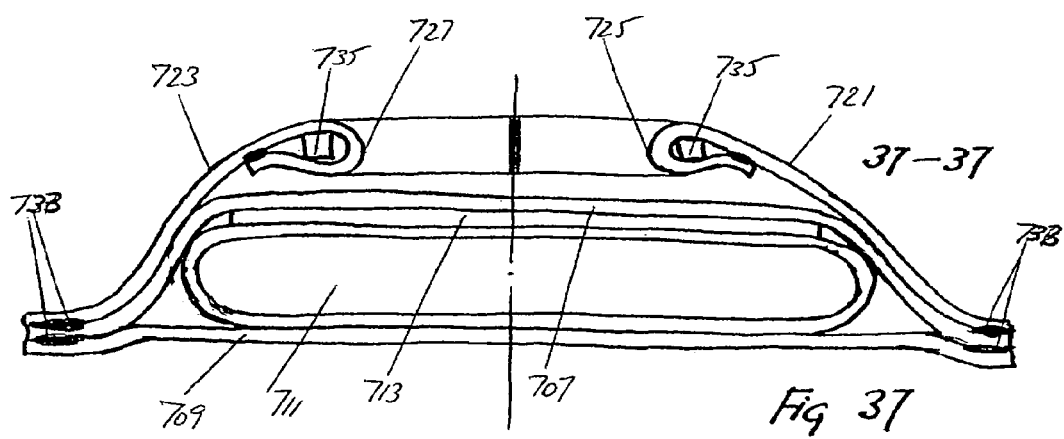
FIG. 37 is a sectional view taken along the line 37—37 of FIG. 35.

Referring to the drawings, first to FIGS. 1–7, there is shown, in FIG. 1, an absorbent article generally designated as 100, in the form of a brief in a stretched position. The term "brief" as used herein is intended to refer to disposable garments worn below the lower part of the torso by incontinent persons and also comprises disposable articles such as baby diapers, adult incontinent underpants, guards and the like articles. The absorbent article 100 comprises a back waist region 101, a front waist region 103 and a crotch region 105. As shown in FIGS. 5, 6, and 7, the absorbent article 100 comprises a liquid pervious top sheet or layer 107 facing the body of the wearer, a liquid impervious backsheet 109 which is usually coextensive with the top layer 107, and an absorbent core or pad 111 disposed between the top sheet 107 and backsheet 109. An acquisition layer 113 between the top sheet 107 and the absorbent layer 111 serves to temporarily retain the body exudates and slowly distribute them through the absorbent pad 111. These layers are sealed to each other to form a composite sheet.

Referring again to FIG. 1, the absorbent article 100 is provided with the fastening means or tabs such as the left fastening tab 115A and the right tab 115B, both attached to the back waist portion 101. These fastening tabs are employed to secure the absorbent article around the body of the wearer. The absorbent article 100 also comprises the leg openings 117,119 through which the legs of the wearer extend when the article is worn.

The uniqueness of the absorbent article of this invention as shown, for example, in FIGS. 1–7, resides in the provision of retaining enclosures for retaining the exudates and preventing the exudates from leaking through the article during its use. In addition, this unique structure provides for longitudinal and lateral forces for improved snug body fit which are particularly effective during body movements when the article is soiled.

As is further shown in FIG. 1, the absorbent article 100 comprises the barrier layer 121 defined by four segments 121A, 121B, 121C and 121D which overlies the absorbent region 110 and form the exudate retaining enclosures A, B, C and D (see FIG. 3). The barrier layer 121 is secured to the inside surface of the absorbent article by a suitable adhesive or by some other suitable means. Each of the segments 121A, 121B, 121C and 121D has an inner (relative to the longitudinal sides of the article) elasticized edge such as the elasticized edges 123A, 123B, 123C and 123D. The elasticized edges 123A and 123B are secured together at 125 while the elasticized edges 123C and 123D are joined together at 127. The elasticized edges are joined together adhesively or may be stitched together if desire. The elasticized edges 123A, 123C can overlap each other to form the dual protection barrier 129 near the leg opening 119 and the elasticized edges 123B and 123D can overlap each other near the leg opening 117 to form a double protection barrier 131. The cutaway view in FIG. 1A illustrates the extension of the elastic edge 123B from a point on the lateral side of the absorbent pad 111 which is substantially perpendicular to the longitudinal axis X—X to a point at the longitudinal side of the absorbent layer.

The barrier layer segments 121A, 121B, 121C and 121D may be fabricated from a vapor pervious non-woven material and may be a single layer or multilayer sheet. Such material is available from First Quality Fibers, Inc., McElhattan, Pa., as 17 GSM (gram per square meter) SMS (spunbond/melt blown/spunbond) non-woven grade 172 BWH.

The other materials used in the construction of the absorbent article of the invention are of the type and variety known in the art and are described in several patents such as, for example, U.S. Pat. No. 4,695,278 and U.S. Pat. No. 4,795,454.

Thus, the liquid pervious top layer 107 is a compliant soft material which is not irritating to the skin. Such material can be made from porous foams, reticulated foams, plastics, natural fibers, such as wood or cotton fibers, synthetic fibers such as polyester or polypropylene fibers, or made from a combination of said materials. A suitable polypropylene material is available from First Quality Fibers, Inc., McElhattan, Pa., as grade 15 ILWH.

The liquid impervious backsheet or layer 109 is preferably manufactured from a thin flexible plastic film such as polyethylene film available from Clopay Plastic Products Company, Cincinnati, Ohio, as grade DH-203.

The absorbent layer 111 may be manufactured from a wide variety of liquid absorbent materials of the type usually used in manufacturing disposable diapers and other absorbent articles. Such materials include comminuted wood pulp, creped cellulose wadding, absorbent foams, absorbent sponges, super absorbent polymers or a combination of said materials.

The acquisition layer 113 is made from a nonwoven material which temporarily retain the exudates and distributes them in the absorbent layer. Such material is available from American Nonwoven Corporation, Columbus, Miss., as grade RB-265-14-B/R.

The construction adhesives employed in the present invention is a hot melt adhesive available from Reynolds, Inc., Greensville, S.C. as Reynolds Code No. 51-942.

The composite sheets formed by the different layers of the absorbent pad are shown in FIGS. 5, 6, and 7 and they are basically the same as the composite sheet structure described in copending application Ser. No. 09/149,265 filed Sep. 8, 1998. Thus, as shown in FIG. 5, the top layer 107 is adhesively secured to the backsheet 109 by the construction adhesive 133. As is also shown in FIGS. 5, 6 and 7, the elastic elements 135 are attached along their lengths to the backsheet 109 by the elastic adhesive 136 (see, e.g., FIG. 5). The elastic adhesive is available from H. B. Fuller of St. Paul, Minn., as type HL-1434-X-ZP.

The embodiment shown in FIGS. 8–13 is basically similar to the embodiment illustrated in FIG. 1. However, the elasticized edges of the barrier layer segments intersect at a point which is spaced away from the lateral edges of the absorbent article. Thus, the absorbent article 200 in FIG. 8 comprises a back waist region 201, a front waist region 203 and the crotch portion 205. As shown in FIGS. 10, 11, 12 and 13, the absorbent article 200 comprises a liquid pervious top sheet or layer 207 facing the body of the wearer, a liquid impervious backsheet 209 which is usually coextensive with the top layer 207, an absorbent core or pad 211 between the layers 207 and 209, and an acquisition layer 213 disposed between the top sheet 207 and the absorbent layer 211. The acquisition layer 213 serves to temporarily retain the body exudates and slowly distribute them through the absorbent pad 211. These layers are sealed to each other to form a composite sheet.

The absorbent article 200 is also provided with the left fastening mean or tab 215A and a right fastening mean or tab 215B, both attached to the backwaist portion 201. As in the embodiment of FIG. 1, the fastening means serve to secure the absorbent article around the body of the wearer. The absorbent article 200 further comprises the leg openings 217, 219 through which the legs of the wearer extend when the article is worn. As in the embodiment shown in FIG. 1, the absorbent article shown in FIG. 8 comprises the barrier layer segments 221A, 221B, 221C and 221D which overlie the absorbent region 210 and form therewith the retaining enclosures $A^1$, $B^1$, $C^1$ and $D^1$, respectively. Each of the segments 221A, 221B, 221C and 221D has an inner elasticized edge such as the elasticized edges 223A, 223B, 223C and 223D. The elasticized edges 223A and 223C cross each other near the leg opening 219, to form the dual protection barrier 229, and the elasticized edges 223B and 223D overlap each other to form the dual protection barrier 231 near the leg opening 217. The elasticized edges 223A and 223B also cross each other near the front lateral edge of the absorbent pad 211 and are secured thereto to form the front double protection barrier 225, and similarly the elasticized edges 223C and 223D cross each other at the opposite (rear) lateral edge of the absorbent region 210 to form a rear double protection barrier 227. These double barrier protection layers assure the integrity of the structure and provide for more improved protection against leakage of the body exudates.

In the remaining embodiments, the structure of the absorbent pad is basically the same as in the embodiments illustrated in FIGS. 1–13 and hence they will only be described briefly. Other features of the absorbent articles in the embodiments illustrated by FIGS. 14, 20, 25 and 29 are also similar as in the previous embodiments except for the barrier layer segments which overlie the absorbent layer. Thus, the absorbent article 300 shown in FIGS. 14–19 has a backwaist portion 301, a front waist portion 303, a crotch portion 305, a liquid pervious top sheet or layer 307, a liquid impervious backsheet 309, an absorbent layer 310, an acquisition layer 315 (see FIGS. 17–19), the fastening means or tabs 315A, 315B, and the leg openings 317, 319. The absorbent article in FIG. 14 also comprises the barrier layer segments 321A, 321B, 321C and 321D which overlie the absorbent region 310 and form therewith the retaining enclosures $A^2$, $B^2$, $C^2$ and $D^2$, respectively. Each of the segments 321A, 321B, 321C and 321D has an inner elasticized edge 323A, 323B, 323C and 323D. The elasticized edges 323A and 323D are secured to each other by glue, mechanically or by stitching such as at 325 in spaced relation to the front lateral edge of the absorbent article, and the elasticized edges 323B and 323C are fixed at the back lateral edge of the absorbent pad, and are spaced apart from each other as in 326 and 327. The elasticized edges 323A and 323C cross each other near the leg opening 317 and define the double protection barrier 329 and, similarly, the elasticized edges 323B and 323D cross each other near the leg opening 317 and define the double protection barrier 331. As in the previous embodiments, these double protection barrier layers assure the integrity of the structure and provide additional protection against leakage of the body exudates.

In the embodiment illustrated in FIGS. 20–24, the absorbent article 400 has a backwaist portion 401, a front waist portion 403, a crotch portion 405, a liquid pervious top sheet or layer 407, a liquid impervious backsheet 409, an absorbent pad 411, an acquisition layer 413, the fastening means or tabs 415A, 415B, and the leg openings 317, 319. The absorbent article in FIG. 20 also comprises the barrier layer segments 421A and 421B having opposed, spaced-apart inner (relative to the lateral side edges of the absorbent article) arch-shaped elasticized edges 423A and 423B which partly overlap and define a generally oval region 410 of the absorbent panel 411. The barrier layer segments 421A, 421B with their respective elasticized edges 423A, 423B define the retaining enclosures $A^3$, $B^3$ which serve to retain the body exudates. The arch-shaped elasticized inner edges 423A and 423B cross one another near the leg openings 417,419 thus forming the double protection barriers 425, 427 for added structural integrity and improved protection against leakage of the body exudate.

The absorbent article shown in FIGS. 25–28 has a backwaist portion 501, a front waist portion 503, a crotch portion 505, a liquid pervious top sheet or layer 507, a liquid impervious backsheet 509, an absorbent pad 511, an acquisition layer 513, the fastening means or tabs 515A, 515B, and the leg openings 517, 519. The absorbent article in FIG. 25 also comprises the barrier layer segments 521, 523 in generally triangular configuration and form the retaining enclosures $A^4$, $B^4$ between the absorbent region 510 and the barrier layer segments 521,523. The barrier layer segments 521,523 have inner elastic edges $521^A$, $523^B$ which are secured together and fixed at 525 in spaced relation to the backwaist lateral edges of the absorbent article. Each of the elastic edges 521A and 523B is fixed to the absorbent article as in 526,527, on the longitudinal side edge the front waist side of the absorbent article.

The absorbent article illustrated in FIGS. 29–32 is basically similar to the embodiment shown in FIG. 25. Thus, the absorbent article 600 in FIG. 29 has a backwaist portion 601, a front waist portion 603, a crotch portion 605, a liquid pervious top sheet or layer 607, a liquid impervious backsheet 609, an absorbent pad 611, an acquisition layer 613, the fastening means or tabs 615A, 615B, and the leg openings 617, 619. The absorbent article in FIG. 29 also comprises the overlying barrier layer segment 621 having an inner elasticized edge 623 which forms a retaining enclosure $A^5$ between the absorbent region 610 and the barrier layer 621. The ends of the elasticized edges 623 are fixed as at 625,627.

Referring to FIGS. 33–37, the absorbent article 700 has a backwaist portion 701, a front waist portion 703, a crotch portion 705, a liquid pervious top sheet or layer 707, a liquid impervious backsheet 709, an absorbent pad or core 711, an acquisition layer 713, the fastening means or tabs 715A, 715B and the leg openings 717,719. The absorbent article 700 also comprises the overlying barrier layer segments 721,723 disposed, respectively, to the left and right of the absorbent region 710. The left barrier layer segment 721 spans substantially the length of the absorbent pad and has a generally convex-shaped (relative to the longitudinal axis Y—Y) inner elasticized edge 725 which is fixed to the absorbent article at 726 and 728, and the right barrier segment 723 spans substantially the length of the absorbent pad and has a generally convex-shaped inner elasticized edge 727 which is also fixed to the absorbent article at 726 and 728. The inner elasticized edge 725,727 define a generally oval region 729 below which the absorbent region 710 is clearly visible. Thus, the left barrier layer segment 721 and its underlying portion of the absorbent region 710 define the exudate retaining enclosure $A^6$, and the right barrier layer segment 723 and its underlying portion of the absorbent region 710 define the exudate retaining enclose $B^6$, both a more clearly shown in FIG. 35.

While the present invention has been described and illustrated with reference to several embodiments with certain degree of specificity, it can be appreciated that other embodiments and modifications are obvious to those skilled in the art based on the detailed description herein without departing from the scope of the invention.

The invention claimed is:

1. An integral disposable elasticized absorbent article providing dual barrier layer protection and having a longitudinal axis and a lateral axis, comprising:
    (a) a topsheet, a backsheet, a waist portion having a front waist portion and a back waist portion, a crotch portion and a pair of spaced apart leg openings;
    (b) an absorbent layer having a longitudinal axis and a horizontal axis disposed between said topsheet and said backsheet, said absorbent layer being defined by two opposed spaced apart longitudinal sides, each longitudinal side having a proximal end, a distal end and a middle portion, and opposed spaced apart proximal and distal lateral ends;
    (c) means for fastening said absorbent article around a waist portion of a wearer of the absorbent article; and
    (d) a pair of elasticized barrier layers selected from the group consisting of
    (d1) a pair of elasticized end barrier layers including;
        (i) a first arch-shaped elasticized barrier layer formed of a pair of opposed leg segments and a generally concave bight segment connecting said leg segments, and having a first of said leg segments attached to said topsheet along a length of the periphery of said absorbent layer between the middle portion and distal end, inclusive, of one of said longitudinal sides, a second of said leg segments opposite said first leg segment attached to said topsheet along a length of the periphery of said absorbent layer between the middle portion and distal end, inclusive, of the other of said longitudinal sides, and said bight segment attached to said topsheet along said distal lateral end of said absorbent layer, thereby forming a first retaining enclosure between said first barrier layer and said topsheet; and (ii) a second arch-shape elasticized barrier layer formed of a pair of opposed leg segments and a generally concave bight segment connecting said leg segments, and having a first of said leg segments attached to said topsheet along a length of the periphery of said absorbent layer between the middle portion and proximal end, inclusive, of said one longitudinal side, a second of said leg segments opposite said first leg segment attached to said topsheet along a length of the periphery of said absorbent layer between the middle portion and proximal end, inclusive, of said other longitudinal side, and said bight segment attached to said topsheet along said proximal lateral end of said absorbent layer, thereby forming a second retaining enclosure between said second barrier layer and said topsheet;

each of said first and second arch-shaped elasticized barrier layers being disposed with the respective free ends of said leg segments intersecting and overlapping the respective free ends of said leg segments of the other of said barrier layers to form in said crotch portion a double barrier layer on said topsheet along the middle portion of each of said longitudinal sides; and (d2) a pair of elasticized side barrier layers including:

(i) a first generally concave elasticized barrier layer having a first end segment attached to said topsheet along a length of the periphery of said absorbent layer between the middle portion and distal end, inclusive, of one of said longitudinal sides, and a second end segment opposite said first end segment attached to said topsheet along a length of the periphery of said absorbent layer between the middle portion and proximal end, inclusive, of said one longitudinal side, and an intermediate segment connecting said first and second end segments attached to said topsheet along said one longitudinal side, thereby forming a first retaining enclosure between said first barrier layer and said topsheet; and (ii) a second generally concave elasticized barrier layer having a first end segment attached to said topsheet along a length of the periphery of said absorbent layer between the middle portion and distal end, inclusive, of the other of said longitudinal sides, a second end segment opposite said first end segment attached to said topsheet along a length of the periphery of said absorbent layer between the middle portion and proximal end, inclusive, of said other longitudinal side, and an intermediate segment connecting said first and second end segments attached to said topsheet along said other longitudinal side, thereby forming a second retaining enclosure between said second barrier layer and said topsheet;

each of said first and second elasticized barrier layers being formed of a pair of generally triangular elements disposed with the respective apices thereof intersecting and overlapping each other to form in said crotch portion a double barrier layer on said topsheet along the middle portions of each of said longitudinal sides.

2. The article of claim 1 wherein said pair of elasticized barrier layers is said pair of elasticized side barrier layers.

3. The article of claim 2 wherein:
one of said first and second end segments of each of said first and second elasticized side barrier layers is attached to said topsheet along one of said proximal and distal ends of said absorbent layer; and
the other of said first and second end segments of each of said first and second elasticized side barrier layers is attached to said topsheet along the other of said proximal and distal ends of said absorbent layer.

4. The article of claim 2 wherein one of said triangular elements of said first elasticized side barrier layer intersects and overlaps a laterally aligned one of said triangular elements of said second elasticized side barrier layers to form a double barrier layer on said top sheet along one of said proximal and distal lateral ends of said absorbent layer.

5. The article of claim 4 forming three double barrier layers.

6. The article of claim 2 wherein each of said triangular elements of said first elasticized side barrier layer intersects and overlaps a respective laterally aligned one of said triangular elements of said second elasticized side barrier layer to form a double barrier layer on said top sheet along each of said proximal and distal lateral ends of said absorbent layer.

7. The article of claim 6 forming four double barrier layers.

8. The article of claim 1 wherein said pair of elasticized barrier layers is said pair of elasticized end barrier layers.

9. The article of claim 2 wherein each of said generally triangular elements forms a generally right triangular element with the hypotenuse of said generally right triangular element being elasticized.

10. The article of claim 9 wherein only said hypotenuse of each said generally right triangular element is elasticized.

11. The article of claim 9 wherein said hypotenuses intercept and overlap each other at points spaced from both said longitudinal sides.

12. The article of claim 8 wherein the inner edges of said leg segments are elasticized.

13. The article of claim 12 wherein only said inner edges of said leg segments are elasticized.

14. The article of claim 8 wherein said inner edges of said leg segments intersect and overlap each other only at points spaced from both said longitudinal sides.

15. The article of claim 8 wherein the inner edges of said bight segments are elasticized and spaced from an adjacent one of said lateral ends.

16. The article of claim 1 wherein each of said elasticized barrier layers has an elasticized inner edge
(i) defining a partially continuous configuration having a discontinuity therein, and
(ii) extending for essentially its entire length non-parallel to said longitudinal axis.

17. The article of claim 1 wherein each of said elasticized barrier layers is a vapor-pervious nonwoven.

18. An integral disposable elasticized absorbent article having a longitudinal axis and a lateral axis, comprising:
(a) a top sheet, a back sheet, a waist portion having a front waist portion and a back waist portion, a crotch portion and a pair of spaced apart leg openings;
(b) an absorbent layer having a longitudinal axis and a horizontal axis disposed between said top sheet and said back sheet, said absorbent layer being defined by two opposed spaced apart longitudinal sides, each longitudinal side having a proximal end, a distal end and a middle portion, and opposed spaced apart proximal and distal lateral ends;

(c) means for fastening said absorbent article around a waist portion of a wearer of the absorbent article; and (d) at least one elasticized barrier layer selected from the group consisting of:
  (i) an arch-shaped elasticized end barrier layer formed of a pair of opposed leg segments and a generally concave bight segment connecting said leg segments, and having a first of said leg segments attached to said top sheet along a length of the periphery of said absorbent layer between the middle portion and distal end, inclusive, of one of said longitudinal sides, a second of said leg segments opposite said first attached to said top sheet along a length of the periphery of said absorbent layer between the middle portion and distal end, inclusive, of the other of said longitudinal sides, and said bight segment attached to said top sheet along said distal lateral end of said absorbent layer, thereby forming a retaining enclosure between said barrier layer and said top sheet;
  (ii) a generally concave elasticized end barrier layer having a first end segment attached to said top sheet along a length of the periphery of said absorbent layer between the middle portion and distal end, inclusive, of one of said longitudinal sides, a second end segment opposite said first end segment attached to said top sheet along a length of the periphery of said absorbent layer between the middle portion and proximal end, inclusive, of the other of said longitudinal sides, and an intermediate segment connecting said first and second end segments attached to said top sheet along one of said lateral ends of said absorbent layer, thereby forming a retaining enclosure between said barrier layer and said top sheet;
  (iii) a generally concave elasticized side barrier layer having a first end segment attached to said top sheet along a length of the periphery of said absorbent layer between the middle portion and distal end, inclusive, of one of said longitudinal sides, and a second end segment opposite said first end segment attached to said top sheet along a length of the periphery of said absorbent layer between the middle portion and proximal end, inclusive, of said one longitudinal side, and an intermediate segment connecting said first and second end segments attached to said top sheet along said one longitudinal side, thereby forming a retaining enclosure between said barrier layer and said top sheet; and
  (iv) combinations thereof; said at least one elasticized barrier layer having an elasticized inner edge
    (A) defining a partially continuous configuration having a discontinuity therein, and
    (B) extending for essentially its entire length non-parallel to said longitudinal axis.

19. The article of claim 18 wherein said at least one elasticized barrier layer is said arch-shaped elasticized end barrier layer.

20. The article of claim 18 wherein said at least one elasticized barrier layer is said generally concave elasticized end barrier layer.

21. The article of claim 18 wherein said at least one elasticized barrier layer is said generally concave elasticized side barrier layer.

22. The article of claim 18 wherein said arch-shaped elasticized end barrier layer of paragraph (i) defines a pair of facing retaining enclosures, said generally concave elasticized end barrier layer of paragraph (ii) defines a single retaining enclosure adjacent said one lateral end of said absorbent layer, and (iii) said generally concave elasticize side barrier layer defines a single retaining enclosure spaced from the other of said longitudinal sides.

* * * * *